US008557585B2

United States Patent
Ha et al.

(10) Patent No.: US 8,557,585 B2
(45) Date of Patent: Oct. 15, 2013

(54) FUSION POLYNUCLEOTIDE FOR BIOSYNTHESIS OF BETA-CAROTENE USING BICISTRONIC GENE EXPRESSION AND METHOD FOR PRODUCING BETA-CAROTENE USING THE SAME

(75) Inventors: Sun Hwa Ha, Gyeonggi-do (KR); Ju Kon Kim, Gyeonggi-do (KR); Ha Rin Jung, Gyeonggi-do (KR); Jung Bong Kim, Gyeonggi-do (KR); Young Mi Kim, Gyeonggi-do (KR); Seok-Cheol Suh, Gyeonggi-do (KR); Liang Ying Shi, Gyeonggi-do (KR); Soon Jong Kweon, Gyeonggi-do (KR); Dong Hern Kim, Gyeonggi-do (KR)

(73) Assignee: Republic of Korea, Rural Development Administration, Suwon, Gyeonggi-Do (KR)

( * ) Notice: Subject to any disclaimer, the term of this patent is extended or adjusted under 35 U.S.C. 154(b) by 694 days.

(21) Appl. No.: 12/675,240

(22) PCT Filed: Aug. 29, 2008

(86) PCT No.: PCT/KR2008/005086
§ 371 (c)(1),
(2), (4) Date: Feb. 25, 2010

(87) PCT Pub. No.: WO2009/028903
PCT Pub. Date: Mar. 5, 2009

(65) Prior Publication Data
US 2010/0299783 A1    Nov. 25, 2010

(30) Foreign Application Priority Data

Aug. 30, 2007  (KR) .......... 10-2007-0087608
Jan. 31, 2008  (KR) .......... 10-2008-0010138

(51) Int. Cl.
C12N 15/82   (2006.01)
C12N 15/10   (2006.01)
C12N 1/20    (2006.01)
A01H 15/00   (2006.01)

(52) U.S. Cl.
USPC ..... 435/468; 435/320.1; 435/419; 435/252.2; 800/320.2; 800/297

(58) Field of Classification Search
None
See application file for complete search history.

(56) References Cited

U.S. PATENT DOCUMENTS 7,663,022 B1 * 2/2010 Hudkins ............... 800/282

FOREIGN PATENT DOCUMENTS

EP        393690 A * 10/1990 ......... C12N 15/52
WO    WO 2007028115 A2 * 3/2007

OTHER PUBLICATIONS

Halpin et al (1999, Plant Journal, 17:453-459).*
Dorokhov et al (2002, PNAS, 99:5301-5306).*
Al-Babili et al (2006, J. of Exp. Botany, 57:1007-1014).*
Ivanov et al, 1997, Virology, 232:32-43.*

* cited by examiner

Primary Examiner — Ashwin Mehta
Assistant Examiner — Jason Deveau Roaen
(74) Attorney, Agent, or Firm — Edwards Wildman Palmer LLP

(57) ABSTRACT

The present invention relates to fusion polynucleotides for biosynthesis of beta-carotene and a method for producing beta-carotene using the same. More particularly, it relates to fusion polynucleotides encoding phytoene synthase, connective sequences of FMDV-derived 2A sequence or internal ribosome entry site (IRES) and carotene desaturase, and a method for producing beta-carotenes using the same. Fusion polynucleotides and the recombinant vector using the same of the present invention have the effect of expression both phytoene synthase gene and carotene desaturase gene stably within cell transformants. Accordingly, fusion polynucleotides of the present invention can be used to regulate the biosynthetic metabolism of plant producing beta-carotene. Furthermore, it can be applied to effectively increase the content of beta-carotene, a useful metabolite.

9 Claims, 11 Drawing Sheets ically active beta-carotene using a multi-cistronic gene expression technique through a fusion polynucleotide comprising both phytoene synthase and carotene desaturase, which enables biosynthesis of biological

SEQUENCE LISTING

```
<160> NUMBER OF SEQ ID NOS: 57

<210> SEQ ID NO 1
<211> LENGTH: 2952
<212> TYPE: DNA
<213> ORGANISM: Artificial Sequence
<220> FEATURE:
<223> OTHER INFORMATION: PAC fusion polynucleotide

<400> SEQUENCE: 1
atgtctgttg ccttgttatg ggttgtttct ccttgtgacg tctcaaacgg gacaggattc        60
ttggtatccg ttcgtgaggg aaaccggatt tttgattcgt cggggcgtag gaatttggcg       120
tgcaatgaga gaatcaagag aggaggtgga aaacaaaggt ggagttttgg ttcttacttg       180
ggaggagcac aaactggaag tggacggaaa ttttctgtac gttctgctat cgtggctact       240
ccggctggag aaatgacgat gtcatcagaa cggatggtat atgatgtggt tttgaggcag       300
gcagccttgg tgaagagaca gctgagatcg accgatgagt tagatgtgaa gaaggatata       360
cctattccgg ggactttggg cttgttgagt gaagcatatg ataggtgtag tgaagtatgt       420
gcagagtacg caaagacgtt ttacttagga acgatgctaa tgactccgga gagaagaaag       480
gctatctggg caatatacgt atggtgcagg agaacagacg aacttgttga tggtccgaat       540
gcatcacaca ttactccggc ggccttagat aggtgggaag acaggctaga agatgttttc       600
agtggacggc catttgacat gctcgatgct gctttgtccg acacagtttc caaatttcca       660
gttgatattc agccattcag agatatgatt gaaggaatgc gtatggactt gaggaagtca       720
agatacagaa acttttgacga actataccta tattgttatt acgttgctgg tacggttggg       780
ttgatgagtg ttccaattat gggcatcgca cctgaatcaa aggcaacaac ggagagcgta       840
tataatgctg ctttggcttt ggggatcgca aatcagctga ccaacatact tagagatgtt       900
ggagaagatg ccagaagagg aagagtctat ttgcctcaag atgaattagc acaggcaggt       960
ctatccgacg aagacatatt tgctggaaga gtgaccgata aatggagaat cttcatgaag      1020
aaacaaattc agagggcaag aaagttcttt gacgaggcag agaaaggagt gaccgaattg      1080
agcgcagcta gtagatggcc tgtgttggca tctctgctgt tgtaccgcag gatactggac      1140
```

```
gagatcgaag ccaatgacta caacaacttc acaaagagag cttatgtgag caaaccaaag    1200
aagttgattg cattacctat tgcatatgca aaatctcttg tgccttctac aagaacactg    1260
cagctcctca acttcgacct cctcaagctc gccggcgacg tcgagagcaa cgacggcccg    1320
ggcatggccc cctccgtgat ggcgtcgtcg gccaccaccg tcgctccctt ccagggctc     1380 aagtccaccg ccggcatgcc cgtcgcccgc cgctccggca actccagctt cggcaacgtc    1440
agcaatggcg gcaggatcag gtgcatgcag gccatggaac caactacggt aattggtgca    1500
ggcttcggtg gcctggcact ggcaattcgt ctacaagctg cggggatccc cgtcttactg    1560
cttgaacaac gtgataaacc cggcggtcgg gcttatgtct acgaggatca ggggtttacc    1620
tttgatgcag gcccgacggt tatcaccgat cccagtgcca ttgaagaact gtttgcactg    1680
gcaggaaaac agttaaaaga gtatgtcgaa ctgctgccgg ttacgccgtt ttaccgcctg    1740
tgttgggagt cagggaaggt ctttaattac gataacgatc aaaccccggct cgaagcgcag   1800 attcagcagt ttaatccccg cgatgtcgaa ggttatcgtc agtttctgga ctattcacgc    1860
gcggtgttta agaaggcta tctaaagctc ggtactgtcc cttttttatc gttcagagac     1920
atgcttcgcg ccgcacctca actggcgaaa ctgcaggcat ggagaagcgt ttacagtaag    1980
gttgccagtt acatcgaaga tgaacatctg cgccaggcgt tttctttcca ctcgctgttg    2040
gtgggcggca atcccttcgc cacctcatcc atttatacgt tgatacacgc gctggagcgt    2100
gagtggggcg tctggtttcc gcgtggcggc accggcgcat tagttcaggg gatgataaag    2160
ctgtttcagg atctgggtgg cgaagtcgtg ttaaacgcca gagtcagcca tatggaaacg    2220
acaggaaaca agattgaagc cgtgcattta gaggacggtc gcaggttcct gacgcaagcc    2280
gtcgcgtcaa atgcagatgt ggttcatacc tatcgcgacc tgttaagcca gcaccctgcc    2340
gcggttaagc agtccaacaa actgcagact aagcgcatga gtaactctct gtttgtgctc    2400
tattttggtt tgaatcacca tcatgatcag ctcgcgcatc acacggtttg tttcggcccg    2460
cgttaccgcg agctgattga cgaaatttt aatcatgatg gcctcgcaga ggacttctca    2520
ctttatctgc acgcgccctg tgtcacggat tcgtcactgg cgcctgaagg ttgcggcagt    2580
tactatgtgt tggcgccggt gccgcattta ggcaccgcga acctcgactg gacggttgag    2640
gggccaaaac tacgcgaccg tatttttgcg taccttgagc agcattacat gcctggctta    2700
cggagtcagc tggtcacgca ccggatgttt acgccgtttg attttcgcga ccagcttaat    2760
gcctatcatg gctcagcctt ttctgtggag cccgttctta cccagagcgc ctggtttcgg    2820
ccgcataacc gcgataaaac cattactaat ctctacctgg tcggcgcagg cacgcatccc    2880
ggcgcaggca ttcctggcgt catcggctcg gcaaaagcga cagcaggttt gatgctggag    2940
gatctgattt ga                                                        2952
```

<210> SEQ ID NO 2
<211> LENGTH: 20
<212> TYPE: PRT
<213> ORGANISM: Artificial Sequence
<220> FEATURE:
<223> OTHER INFORMATION: self-cleavage 2A amino acid sequence

<400> SEQUENCE: 2

Gln Leu Leu Asn Phe Asp Leu Leu Lys Leu Ala Gly Asp Val Glu Ser
 1               5                  10                  15

Asn Pro Gly Pro
            20

<210> SEQ ID NO 3
<211> LENGTH: 66
<212> TYPE: DNA
<213> ORGANISM: Artificial Sequence
<220> FEATURE:
<223> OTHER INFORMATION: 2A nucleotide sense sequence

<400> SEQUENCE: 3

```
ctgcagctcc tcaacttcga cctcctcaag ctcgccggcg acgtcgagag caacgacggc    60
ccgggc                                                                66
```

<210> SEQ ID NO 4
<211> LENGTH: 66
<212> TYPE: DNA
<213> ORGANISM: Artificial Sequence
<220> FEATURE:
<223> OTHER INFORMATION: 2A nucleotide antisense sequence

<400> SEQUENCE: 4

```
gcccgggccg tcgttgctct cgacgtcgcc ggcgagcttg aggaggtgga agttgaggag    60
ctgcag                                                                66
```

<210> SEQ ID NO 5
<211> LENGTH: 419
<212> TYPE: PRT
<213> ORGANISM: Capsicum annuum

<400> SEQUENCE: 5

```
Met Ser Val Ala Leu Leu Trp Val Val Ser Pro Cys Asp Val Ser Asn
 1               5                  10                  15

Gly Thr Gly Phe Leu Val Ser Val Arg Glu Gly Asn Arg Ile Phe Asp
            20                  25                  30

Ser Ser Gly Arg Arg Asn Leu Ala Cys Asn Glu Arg Ile Lys Arg Gly
        35                  40                  45

Gly Gly Lys Gln Arg Trp Ser Phe Gly Ser Tyr Leu Gly Gly Ala Gln
    50                  55                  60

Thr Gly Ser Gly Arg Lys Phe Ser Val Arg Ser Ala Ile Val Ala Thr
65                  70                  75                  80

Pro Ala Gly Glu Met Thr Met Ser Ser Glu Arg Met Val Tyr Asp Val
                85                  90                  95

Val Leu Arg Gln Ala Ala Leu Val Lys Arg Gln Leu Arg Ser Thr Asp
            100                 105                 110

Glu Leu Asp Val Lys Lys Asp Ile Pro Ile Pro Gly Thr Leu Gly Leu
        115                 120                 125

Leu Ser Glu Ala Tyr Asp Arg Cys Ser Glu Val Cys Ala Glu Tyr Ala
    130                 135                 140

Lys Thr Phe Tyr Leu Gly Thr Met Leu Met Thr Pro Glu Arg Arg Lys
145                 150                 155                 160

Ala Ile Trp Ala Ile Tyr Val Trp Cys Arg Arg Thr Asp Glu Leu Val
                165                 170                 175

Asp Gly Pro Asn Ala Ser His Ile Thr Pro Ala Ala Leu Asp Arg Trp
            180                 185                 190

Glu Asp Arg Leu Glu Asp Val Phe Ser Gly Arg Pro Phe Asp Met Leu
        195                 200                 205

Asp Ala Ala Leu Ser Asp Thr Val Ser Lys Phe Pro Val Asp Ile Gln
    210                 215                 220

Pro Phe Arg Asp Met Ile Glu Gly Met Arg Met Asp Leu Arg Lys Ser
225                 230                 235                 240
```

```
               Arg Tyr Arg Asn Phe Asp Glu Leu Tyr Leu Tyr Cys Tyr Tyr Val Ala
                           245                 250                 255

Gly Thr Val Gly Leu Met Ser Val Pro Ile Met Gly Ile Ala Pro Glu
                       260                 265                 270

Ser Lys Ala Thr Thr Glu Ser Val Tyr Asn Ala Ala Leu Ala Leu Gly
                       275                 280                 285

Ile Ala Asn Gln Leu Thr Asn Ile Leu Arg Asp Val Gly Glu Asp Ala
                       290                 295                 300

Arg Arg Gly Arg Val Tyr Leu Pro Gln Asp Glu Leu Ala Gln Ala Gly
               305                 310                 315                 320

Leu Ser Asp Glu Asp Ile Phe Ala Gly Arg Val Thr Asp Lys Trp Arg
                               325                 330                 335

Ile Phe Met Lys Lys Gln Ile Gln Arg Ala Arg Lys Phe Phe Asp Glu
                           340                 345                 350

Ala Glu Lys Gly Val Thr Glu Leu Ser Ala Ala Ser Arg Trp Pro Val
                       355                 360                 365

Leu Ala Ser Leu Leu Leu Tyr Arg Arg Ile Leu Asp Glu Ile Glu Ala
                       370                 375                 380

Asn Asp Tyr Asn Asn Phe Thr Lys Arg Ala Tyr Val Ser Lys Pro Lys
               385                 390                 395                 400

Lys Leu Ile Ala Leu Pro Ile Ala Tyr Ala Lys Ser Leu Val Pro Ser
                               405                 410                 415

Thr Arg Thr

<210> SEQ ID NO 6
               <211> LENGTH: 1260
               <212> TYPE: DNA
               <213> ORGANISM: Capsicum annuum

<400> SEQUENCE: 6
atgtctgttg ccttgttatg ggttgtttct ccttgtgacg tctcaaacgg gacaggattc     60
ttggtatccg ttcgtgaggg aaaccggatt tttgattcgt cggggcgtag gaatttggcg    120
tgcaatgaga gaatcaagag aggaggtgga aaacaaaggt ggagttttgg ttcttacttg    180
ggaggagcac aaactggaag tggacggaaa ttttctgtac gttctgctat cgtggctact    240
ccggctggag aaatgacgat gtcatcagaa cggatggtat atgatgtggt tttgaggcag    300
gcagccttgg tgaagagaca gctgagatcg accgatgagt tagatgtgaa gaaggatata    360
cctattccgg ggactttggg cttgttgagt gaagcatatg ataggtgtag tgaagtatgt    420
gcagagtacg caaagacgtt ttacttagga acgatgctaa tgactccgga gaagaaaag     480 gctatctggg caatatacgt atggtgcagg agaacagacg aacttgttga tggtccgaat    540
gcatcacaca ttactccggc ggccttagat aggtgggaag acaggctaga agatgttttc    600
agtggacggc catttgacat gctcgatgct gctttgtccg acacagtttc caaatttcca    660
gttgatattc agccattcag agatatgatt gaaggaatgc gtatggactt gaggaagtca    720
agatacagaa actttgacga actataccta tattgttatt acgttgctgg tacggttggg    780
ttgatgagtg ttccaattat gggcatcgca cctgaatcaa aggcaacaac ggagagcgta    840
tataatgctg ctttggcttt ggggatcgca aatcagctga ccaacatact tagagatgtt    900
ggagaagatg ccagaagagg aagagtctat ttgcctcaag atgaattagc acaggcaggt    960
ctatccgacg aagacatatt tgctggaaga gtgaccgata atggagaat cttcatgaag     1020 aaacaaattc agagggcaag aaagttcttt gacgaggcag agaaaggagt gaccgaattg   1080
agcgcagcta gtagatggcc tgtgttggca tctctgctgt tgtaccgcag gatactggac   1140
```

```
gagatcgaag ccaatgacta caacaacttc acaaagagag cttatgtgag caaaccaaag    1200
aagttgattg cattacctat tgcatatgca aaatctcttg tgccttctac aagaacatga    1260
```

<210> SEQ ID NO 7
<211> LENGTH: 492
<212> TYPE: PRT
<213> ORGANISM: Erwinia uredovora

<400> SEQUENCE: 7

```
Met Glu Pro Thr Thr Val Ile Gly Ala Gly Phe Gly Gly Leu Ala Leu
 1               5                  10                  15

Ala Ile Arg Leu Gln Ala Ala Gly Ile Pro Val Leu Leu Leu Glu Gln
             20                  25                  30

Arg Asp Lys Pro Gly Gly Arg Ala Tyr Val Tyr Glu Asp Gln Gly Phe
         35                  40                  45

Thr Phe Asp Ala Gly Pro Thr Val Ile Thr Asp Pro Ser Ala Ile Glu
     50                  55                  60

Glu Leu Phe Ala Leu Ala Gly Lys Gln Leu Lys Glu Tyr Val Glu Leu
 65                  70                  75                  80

Leu Pro Val Thr Pro Phe Tyr Arg Leu Cys Trp Glu Ser Gly Lys Val
                 85                  90                  95

Phe Asn Tyr Asp Asn Asp Gln Thr Arg Leu Glu Ala Gln Ile Gln Gln
            100                 105                 110

Phe Asn Pro Arg Asp Val Glu Gly Tyr Arg Gln Phe Leu Asp Tyr Ser
        115                 120                 125

Arg Ala Val Phe Lys Glu Gly Tyr Leu Lys Leu Gly Thr Val Pro Phe
    130                 135                 140

Leu Ser Phe Arg Asp Met Leu Arg Ala Ala Pro Gln Leu Ala Lys Leu
145                 150                 155                 160

Gln Ala Trp Arg Ser Val Tyr Ser Lys Val Ala Ser Tyr Ile Glu Asp
                165                 170                 175

Glu His Leu Arg Gln Ala Phe Ser Phe His Ser Leu Leu Val Gly Gly
            180                 185                 190

Asn Pro Phe Ala Thr Ser Ser Ile Tyr Thr Leu Ile His Ala Leu Glu
        195                 200                 205

Arg Glu Trp Gly Val Trp Phe Pro Arg Gly Gly Thr Gly Ala Leu Val
    210                 215                 220

Gln Gly Met Ile Lys Leu Phe Gln Asp Leu Gly Gly Glu Val Val Leu
225                 230                 235                 240

Asn Ala Arg Val Ser His Met Glu Thr Thr Gly Asn Lys Ile Glu Ala
                245                 250                 255

Val His Leu Glu Asp Gly Arg Arg Phe Leu Thr Gln Ala Val Ala Ser
            260                 265                 270

Asn Ala Asp Val Val His Thr Tyr Arg Asp Leu Leu Ser Gln His Pro
        275                 280                 285

Ala Ala Val Lys Gln Ser Asn Lys Leu Gln Thr Lys Arg Met Ser Asn
    290                 295                 300

Ser Leu Phe Val Leu Tyr Phe Gly Leu Asn His His His Asp Gln Leu
305                 310                 315                 320

Ala His His Thr Val Cys Phe Gly Pro Arg Tyr Arg Glu Leu Ile Asp
                325                 330                 335

Glu Ile Phe Asn His Asp Gly Leu Ala Glu Asp Phe Ser Leu Tyr Leu
            340                 345                 350

His Ala Pro Cys Val Thr Asp Ser Ser Leu Ala Pro Glu Gly Cys Gly
```

```
              355                 360                 365
Ser Tyr Tyr Val Leu Ala Pro Val Pro His Leu Gly Thr Ala Asn Leu
    370                 375                 380

Asp Trp Thr Val Glu Gly Pro Lys Leu Arg Asp Arg Ile Phe Ala Tyr
385                 390                 395                 400

Leu Glu Gln His Tyr Met Pro Gly Leu Arg Ser Gln Leu Val Thr His
                405                 410                 415

Arg Met Phe Thr Pro Phe Asp Phe Arg Asp Gln Leu Asn Ala Tyr His
                420                 425                 430

Gly Ser Ala Phe Ser Val Glu Pro Val Leu Thr Gln Ser Ala Trp Phe
            435                 440                 445

Arg Pro His Asn Arg Asp Lys Thr Ile Thr Asn Leu Tyr Leu Val Gly
        450                 455                 460

Ala Gly Thr His Pro Gly Ala Gly Ile Pro Gly Val Ile Gly Ser Ala
465                 470                 475                 480

Lys Ala Thr Ala Gly Leu Met Leu Glu Asp Leu Ile
                485                 490

<210> SEQ ID NO 8
<211> LENGTH: 1479
<212> TYPE: DNA
<213> ORGANISM: Erwinia uredovora

<400> SEQUENCE: 8
atggaaccaa ctacggtaat tggtgcaggc ttcggtggcc tggcactggc aattcgtcta      60
caagctgcgg ggatccccgt cttactgctt gaacaacgtg ataaacccgg cggtcgggct     120
tatgtctacg aggatcaggg gtttaccttt gatgcaggcc cgacggttat caccgatccc     180
agtgccattg aagaactgtt tgcactggca ggaaaacagt taaagagta tgtcgaactg     240 ctgccggtta cgccgttta ccgcctgtgt gggagtcag ggaaggtctt taattacgat     300
aacgatcaaa cccggctcga agcgcagatt cagcagttta tccccgcga tgtcgaaggt     360 tatcgtcagt ttctggacta ttcacgcgcg gtgtttaaag aaggctatct aaagctcggt     420
actgtccctt ttttatcgtt cagagacatg cttcgcgccg cacctcaact ggcgaaactg     480
caggcatgga gaagcgttta cagtaaggtt gccagttaca tcgaagatga acatctgcgc     540
caggcgtttt ctttccactc gctgttggtg ggcggcaatc ccttcgccac ctcatccatt     600
tatacgttga tacacgcgct ggagcgtgag tggggcgtct ggtttccgcg tggcggcacc     660
ggcgcattag ttcaggggat gataaagctg tttcaggatc tgggtggcga agtcgtgtta     720
aacgccagag tcagccatat ggaaacgaca ggaaacaaga ttgaagccgt gcatttagag     780
gacggtcgca ggttcctgac gcaagccgtc gcgtcaaatg cagatgtggt tcataccctat     840 cgcgacctgt taagccagca ccctgccgcg gttaagcagt ccaacaaact gcagactaag     900
cgcatgagta actctctgtt tgtgctctat tttggtttga atcaccatca tgatcagctc     960
gcgcatcaca cggtttgttt cggcccgcgt taccgcgagc tgattgacga aatttttaat    1020
catgatggcc tcgcagagga cttctcactt tatctgcacg cgccctgtgt cacggattcg    1080
tcactggcgc ctgaaggttg cggcagttac tatgtgttgg cgccggtgcc gcatttaggc    1140
accgcgaacc tcgactggac ggttgagggg ccaaaactac gcgaccgtat ttttgcgtac    1200
cttgagcagc attacatgcc tggcttacgg agtcagctgg tcacgcaccg atgtttacg    1260 ccgtttgatt ttcgcgacca gcttaatgcc tatcatggct cagccttttc tgtggagccc    1320
gttcttaccc agagcgcctg gtttcggccg cataaccgcg ataaaaccat tactaatctc    1380
```

```
tacctggtcg gcgcaggcac gcatcccggc gcaggcattc ctggcgtcat cggctcggca   1440
aaagcgacag caggtttgat gctggaggat ctgatttga                          1479
```

<210> SEQ ID NO 9
<211> LENGTH: 24
<212> TYPE: DNA
<213> ORGANISM: Artificial Sequence
<220> FEATURE:
<223> OTHER INFORMATION: psy-fw primer

<400> SEQUENCE: 9

```
atgtctgttg ccttgttatg ggtt                                          24
```

<210> SEQ ID NO 10
<211> LENGTH: 24
<212> TYPE: DNA
<213> ORGANISM: Artificial Sequence
<220> FEATURE:
<223> OTHER INFORMATION: psy-rv primer

<400> SEQUENCE: 10

```
tcatgttctt gtagaaggca caag                                          24
```

<210> SEQ ID NO 11
<211> LENGTH: 24
<212> TYPE: DNA
<213> ORGANISM: Artificial Sequence
<220> FEATURE:
<223> OTHER INFORMATION: CrtI-fw primer

<400> SEQUENCE: 11

```
atgaaaccaa ctacggtaat tggt                                          24
```

<210> SEQ ID NO 12
<211> LENGTH: 24
<212> TYPE: DNA
<213> ORGANISM: Artificial Sequence
<220> FEATURE:
<223> OTHER INFORMATION: CrtI-rv primer

<400> SEQUENCE: 12

```
tcaaatcaga tcctccagca tcaa                                          24
```

<210> SEQ ID NO 13
<211> LENGTH: 26
<212> TYPE: DNA
<213> ORGANISM: Artificial Sequence
<220> FEATURE:
<223> OTHER INFORMATION: 5H-psy primer

<400> SEQUENCE: 13

```
ccgaagctta tgtctgttgc cttgtt                                        26
```

<210> SEQ ID NO 14
<211> LENGTH: 26
<212> TYPE: DNA
<213> ORGANISM: Artificial Sequence
<220> FEATURE:
<223> OTHER INFORMATION: 3P-Psy primer

<400> SEQUENCE: 14

```
ccgctgcagt gttcttgtag aaggca                                        26
```

<210> SEQ ID NO 15
<211> LENGTH: 26
<212> TYPE: DNA

```
<213> ORGANISM: Artificial Sequence
<220> FEATURE:
<223> OTHER INFORMATION: 5P-Tp primer

<400> SEQUENCE: 15
ccgctgcaga tggcccctc cgtgat                                           26

<210> SEQ ID NO 16
<211> LENGTH: 25
<212> TYPE: DNA
<213> ORGANISM: Artificial Sequence
<220> FEATURE:
<223> OTHER INFORMATION: 3Nc-Tp primer

<400> SEQUENCE: 16
ccgccatggc ctgcatgcac ctgat                                           25

<210> SEQ ID NO 17
<211> LENGTH: 26
<212> TYPE: DNA
<213> ORGANISM: Artificial Sequence
<220> FEATURE:
<223> OTHER INFORMATION: 5Nc-CrtI primer

<400> SEQUENCE: 17
ccgccatgga accaactacg gtaatt                                          26

<210> SEQ ID NO 18
<211> LENGTH: 26
<212> TYPE: DNA
<213> ORGANISM: Artificial Sequence
<220> FEATURE:
<223> OTHER INFORMATION: 3Ap-CrtI primer

<400> SEQUENCE: 18
ccggggccct caaatcagat cctcca                                          26

<210> SEQ ID NO 19
<211> LENGTH: 27
<212> TYPE: DNA
<213> ORGANISM: Artificial Sequence
<220> FEATURE:
<223> OTHER INFORMATION: 5Sm-TpCrtI primer

<400> SEQUENCE: 19
ccgcccgggc atggcccct ccgtgat                                          27

<210> SEQ ID NO 20
<211> LENGTH: 26
<212> TYPE: DNA
<213> ORGANISM: Artificial Sequence
<220> FEATURE:
<223> OTHER INFORMATION: 3Xb-TpCrtI

<400> SEQUENCE: 20
ccgtctagat caaatcagat cctcca                                          26

<210> SEQ ID NO 21
<211> LENGTH: 29
<212> TYPE: DNA
<213> ORGANISM: Artificial Sequence
<220> FEATURE:
<223> OTHER INFORMATION: PAC-B1 primer

<400> SEQUENCE: 21
aaaaagcagg ctatgtctgt tgccttgtt                                       29
```

```
<210> SEQ ID NO 22
<211> LENGTH: 30
<212> TYPE: DNA
<213> ORGANISM: Artificial Sequence
<220> FEATURE:
<223> OTHER INFORMATION: PAC-B2 primer

<400> SEQUENCE: 22
agaaagctgg gtgtcaaatc agatcctcca                                      30

<210> SEQ ID NO 23
<211> LENGTH: 29
<212> TYPE: DNA
<213> ORGANISM: Artificial Sequence
<220> FEATURE:
<223> OTHER INFORMATION: attB1 primer

<400> SEQUENCE: 23
ggggacaagt ttgtacaaaa aagcaggct                                       29

<210> SEQ ID NO 24
<211> LENGTH: 29
<212> TYPE: DNA
<213> ORGANISM: Artificial Sequence
<220> FEATURE:
<223> OTHER INFORMATION: attB2 primer

<400> SEQUENCE: 24
ggggaccact ttgtacaaga aagctgggt                                       29

<210> SEQ ID NO 25
<211> LENGTH: 18
<212> TYPE: DNA
<213> ORGANISM: Artificial Sequence
<220> FEATURE:
<223> OTHER INFORMATION: Psy-CT-Fw primer

<400> SEQUENCE: 25
gagatcgaag ccaatgac                                                   18

<210> SEQ ID NO 26
<211> LENGTH: 18
<212> TYPE: DNA
<213> ORGANISM: Artificial Sequence
<220> FEATURE:
<223> OTHER INFORMATION: CrtI-NT-Rv primer

<400> SEQUENCE: 26
gaagcctgca ccaattac                                                   18

<210> SEQ ID NO 27
<211> LENGTH: 22
<212> TYPE: DNA
<213> ORGANISM: Artificial Sequence
<220> FEATURE:
<223> OTHER INFORMATION: PAIC-F1 primer

<400> SEQUENCE: 27
atgtctgttg ccttgttatg gg                                              22

<210> SEQ ID NO 28
<211> LENGTH: 19
<212> TYPE: DNA
<213> ORGANISM: Artificial Sequence
<220> FEATURE:
<223> OTHER INFORMATION: PAIC-R1 primer
```

```
<400> SEQUENCE: 28
tcaatcagat cctccagca                                                19

<210> SEQ ID NO 29
<211> LENGTH: 18
<212> TYPE: DNA
<213> ORGANISM: Artificial Sequence
<220> FEATURE:
<223> OTHER INFORMATION: Glu-F2203 primer

<400> SEQUENCE: 29
ccgagcccag gttcaagt                                                 18

<210> SEQ ID NO 30
<211> LENGTH: 21
<212> TYPE: DNA
<213> ORGANISM: Artificial Sequence
<220> FEATURE:
<223> OTHER INFORMATION: Glu-R2552 primer

<400> SEQUENCE: 30
aagaggattc cgccacatta t                                             21

<210> SEQ ID NO 31
<211> LENGTH: 150
<212> TYPE: DNA
<213> ORGANISM: crucifer-infecting Tobamovirus

<400> SEQUENCE: 31
acgaattcgt cgattcggtt gcagcattta aagcggttga caactttaaa agaaggaaaa     60
agaaggttga agaaaagggt gtagtaagta agtataagta cagaccggag aagtacgccg    120
gtcctgattc gtttaatttg aaagaagaaa                                    150

<210> SEQ ID NO 32
<211> LENGTH: 53
<212> TYPE: DNA
<213> ORGANISM: crucifer-infecting Tobamovirus

<400> SEQUENCE: 32
acgaattcgt cgattcggtt gcagcattta aagcggttga caactttaaa aga           53

<210> SEQ ID NO 33
<211> LENGTH: 53
<212> TYPE: DNA
<213> ORGANISM: crucifer-infecting Tobamovirus

<400> SEQUENCE: 33
actcacccct ttcttcaac cttcttttc cttcttttaa agttgtcaac cgc              53

<210> SEQ ID NO 34
<211> LENGTH: 54
<212> TYPE: DNA
<213> ORGANISM: crucifer-infecting Tobamovirus

<400> SEQUENCE: 34
gttgaagaaa agggtgtagt aagtaagtat aagtacagac cggagaagta cgcc           54

<210> SEQ ID NO 35
<211> LENGTH: 56
<212> TYPE: DNA
<213> ORGANISM: crucifer-infecting Tobamovirus

<400> SEQUENCE: 35
```

```
tttcttctttt caaattaaac gaatcaggac cggcgtactt ctccggtctg tactta        56
```

```
<210> SEQ ID NO 36
<211> LENGTH: 26
<212> TYPE: DNA
<213> ORGANISM: Oryza sativa

<400> SEQUENCE: 36
ccgctgcaga tggccccctc cgtgat                                           26
```

```
<210> SEQ ID NO 37
<211> LENGTH: 25
<212> TYPE: DNA
<213> ORGANISM: Oryza sativa

<400> SEQUENCE: 37
ccgccatggc ctgcatgcac ctgat                                            25
```

```
<210> SEQ ID NO 38
<211> LENGTH: 26
<212> TYPE: DNA
<213> ORGANISM: Erwinia uredovora

<400> SEQUENCE: 38
ccgccatgga accaactacg gtaatt                                           26
```

```
<210> SEQ ID NO 39
<211> LENGTH: 26
<212> TYPE: DNA
<213> ORGANISM: Erwinia uredovora

<400> SEQUENCE: 39
ccggggccct caaatcagat cctcca                                           26
```

```
<210> SEQ ID NO 40
<211> LENGTH: 26
<212> TYPE: DNA
<213> ORGANISM: crucifer-infecting Tobamovirus

<400> SEQUENCE: 40
ccggagctca cgaattcgtc gattcg                                           26
```

```
<210> SEQ ID NO 41
<211> LENGTH: 36
<212> TYPE: DNA
<213> ORGANISM: crucifer-infecting Tobamovirus

<400> SEQUENCE: 41
ccggagctcg gatcctttct tctttcaaat taaacg                                36
```

```
<210> SEQ ID NO 42
<211> LENGTH: 3077
<212> TYPE: DNA
<213> ORGANISM: Artificial Sequence
<220> FEATURE:
<223> OTHER INFORMATION: Fusion PIC gene comprising phytoene synthase,
      IRES and carotene desaturase

<400> SEQUENCE: 42
atgtctgttg ccttgttatg ggttgtttct ccttgtgacg tctcaaacgg gacaggattc      60
ttggtatccg ttcgtgaggg aaaccggatt tttgattcgt cggggcgtag gaatttggcg     120
tgcaatgaga gaatcaagag aggaggtgga aaacaaaggt ggagttttgg ttcttacttg     180
ggaggagcac aaactggaag tggacggaaa ttttctgtac gttctgctat cgtggctact     240
```

```
ccggctggag aaatgacgat gtcatcagaa cggatggtat atgatgtggt tttgaggcag    300
gcagccttgg tgaagagaca gctgagatcg accgatgagt tagatgtgaa gaaggatata    360
cctattccgg ggactttggg cttgttgagt gaagcatatg ataggtgtag tgaagtatgt    420
gcagagtacg caaagacgtt ttacttagga acgatgctaa tgactccgga gagaagaaag    480
gctatctggg caatatacgt atggtgcagg agaacagacg aacttgttga tggtccgaat    540
gcatcacaca ttactccggc ggccttagat aggtgggaag acaggctaga agatgttttc    600
agtggacggc catttgacat gctcgatgct gctttgtccg acacagtttc caaatttcca    660
gttgatattc agccattcag agatatgatt gaaggaatgc gtatggactt gaggaagtca    720
agatacagaa actttgacga actataccta tattgttatt acgttgctgg tacggttggg    780
ttgatgagtg ttccaattat gggcatcgca cctgaatcaa aggcaacaac ggagagcgta    840
tataatgctg ctttggcttt ggggatcgca aatcagctga ccaacatact tagagatgtt    900
ggagaagatg ccagaagagg aagagtctat ttgcctcaag atgaattagc acaggcaggt    960
ctatccgacg aagacatatt tgctggaaga gtgaccgata aatggagaat cttcatgaag   1020
aaacaaattc agagggcaag aaagttcttt gacgaggcag agaaaggagt gaccgaattg   1080
agcgcagcta gtagatggcc tgtgttggca tctctgctgt tgtaccgcag gatactggac   1140
gagatcgaag ccaatgacta caacaacttc acaaagagag cttatgtgag caaaccaaag   1200
aagttgattg cattacctat tgcatatgca aaatctcttg tgccttctac aagaacatga   1260
aagccgaatt cgtcgattcg gttgcagcat ttaaagcggt tgacaacttt aaaagaagga   1320
aaagaaggt tgaagaaaag ggtgtagtaa gtaagtataa gtacagaccg gagaagtacg   1380
ccggtcctga ttcgtttaat ttgaaagaag aaaggatccg agctctccca tatggtcgac   1440
ctgcagagat ggcccctcc gtgatggcgt cgtcggccac caccgtcgct cccttccagg   1500
ggctcaagtc caccgccggc atgcccgtcg cccgccgctc cggcaactcc agcttcggca   1560
acgtcagcaa tggcggcagg atcaggtgca tgcaggccat ggaaccaact acggtaattg   1620
gtgcaggctt cggtggcctg gcactggcaa ttcgtctaca agctgcgggg atccccgtct   1680
tactgcttga caacgtgat aaacccggcg gtcgggctta tgtctacgag gatcaggggt   1740
ttacctttga tgcaggcccg acggttatca ccgatcccag tgccattgaa gaactgtttg   1800
cactggcagg aaaacagtta aaagagtatg tcgaactgct gccggttacg ccgttttacc   1860
gcctgtgttg ggagtcaggg aaggtctttta attacgataa cgatcaaacc cggctcgaag   1920
cgcagattca gcagtttaat ccccgcgatg tcgaaggtta tcgtcagttt ctggactatt   1980
cacgcgcggt gtttaaagaa ggctatctaa agctcggtac tgtcccttt ttatcgttca   2040
gagacatgct tcgcgccgca cctcaactgg cgaaactgca ggcatggaga agcgtttaca   2100
gtaaggttgc cagttacatc gaagatgaac atctgcgcca ggcgttttct ttccactcgc   2160
tgttggtggg cggcaatccc ttcgccacct catccattta tacgttgata cacgcgctgg   2220
agcgtgagtg gggcgtctgg tttccgcgtg gcggcaccgg cgcattagtt caggggatga   2280
taaagctgtt tcaggatctg ggtggcgaag tcgtgttaaa cgccagagtc agccatatgg   2340
aaacgacagg aaacaagatt gaagccgtgc atttagagga cggtcgcagg ttcctgacgc   2400
aagccgtcgc gtcaaatgca gatgtggttc atacctatcg cgacctgtta agccagcacc   2460
ctgccgcggt taagcagtcc aacaaactgc agactaagcg catgagtaac tctctgtttg   2520
tgctctattt tggtttgaat caccatcatg atcagctcgc gcatcacacg gtttgtttcg   2580
gcccgcgtta ccgcgagctg attgacgaaa ttttttaatca tgatggcctc gcagaggact   2640
```

```
tctcacttta tctgcacgcg ccctgtgtca cggattcgtc actggcgcct gaaggttgcg    2700
gcagttacta tgtgttggcg ccggtgccgc atttaggcac cgcgaacctc gactggacgg    2760
ttgaggggcc aaaactacgc gaccgtattt ttgcgtacct tgagcagcat tacatgcctg    2820
gcttacggag tcagctggtc acgcaccgga tgtttacgcc gtttgatttt cgcgaccagc    2880
ttaatgccta tcatggctca gccttttctg tggagcccgt tcttacccag agcgcctggt    2940
ttcggccgca taaccgcgat aaaaccatta ctaatctcta cctggtcggc gcaggcacgc    3000
atcccggcgc aggcattcct ggcgtcatcg gctcggcaaa agcgacagca ggtttgatgc    3060
tggaggatct gatttga                                                   3077

<210> SEQ ID NO 43
<211> LENGTH: 29
<212> TYPE: DNA
<213> ORGANISM: Artificial Sequence
<220> FEATURE:
<223> OTHER INFORMATION: the specific primer for amplifying the PIC gene

<400> SEQUENCE: 43
aaaaagcagg ctatgtctgt tgccttgtt                                       29

<210> SEQ ID NO 44
<211> LENGTH: 29
<212> TYPE: DNA
<213> ORGANISM: Artificial Sequence
<220> FEATURE:
<223> OTHER INFORMATION: the specific primer for amplifying the PIC gene

<400> SEQUENCE: 44
agaaagctgg gttcaaatca gatcctcca                                       29

<210> SEQ ID NO 45
<211> LENGTH: 29
<212> TYPE: DNA
<213> ORGANISM: Artificial Sequence
<220> FEATURE:
<223> OTHER INFORMATION: the specific primer including specific
      recombined nucleic acid of bacteria

<400> SEQUENCE: 45
ggggacaagt ttgtacaaaa aagcaggct                                       29

<210> SEQ ID NO 46
<211> LENGTH: 29
<212> TYPE: DNA
<213> ORGANISM: Artificial Sequence
<220> FEATURE:
<223> OTHER INFORMATION: the specific primer including specific
      recombined nucleic acid of bacteria

<400> SEQUENCE: 46
ggggaccact ttgtacaaga aagctgggt                                       29

<210> SEQ ID NO 47
<211> LENGTH: 18
<212> TYPE: DNA
<213> ORGANISM: Artificial Sequence
<220> FEATURE:
<223> OTHER INFORMATION: the specific primer including CrTMV IRES

<400> SEQUENCE: 47
gagatcgaag ccaatgac                                                   18
```

```
<210> SEQ ID NO 48
<211> LENGTH: 18
<212> TYPE: DNA
<213> ORGANISM: Artificial Sequence
<220> FEATURE:
<223> OTHER INFORMATION: the specific primer including CrTMV IRES

<400> SEQUENCE: 48
gaagcctgca ccaattac                                                       18

<210> SEQ ID NO 49
<211> LENGTH: 24
<212> TYPE: DNA
<213> ORGANISM: Capsicum annuum

<400> SEQUENCE: 49
atgtctgttg ccttgttatg ggtt                                                24

<210> SEQ ID NO 50
<211> LENGTH: 24
<212> TYPE: DNA
<213> ORGANISM: Capsicum annuum

<400> SEQUENCE: 50
tcatgttctt gtagaaggca caag                                                24

<210> SEQ ID NO 51
<211> LENGTH: 27
<212> TYPE: DNA
<213> ORGANISM: Artificial Sequence
<220> FEATURE:
<223> OTHER INFORMATION: the specific primer for amplifying Tp CrtI gene

<400> SEQUENCE: 51
ccgcccgggc atggcccect ccgtgat                                             27

<210> SEQ ID NO 52
<211> LENGTH: 26
<212> TYPE: DNA
<213> ORGANISM: Artificial Sequence
<220> FEATURE:
<223> OTHER INFORMATION: the specific primer for amplifying Tp CrtI gene

<400> SEQUENCE: 52
ccgtctagat caaatcagat cctcca                                              26

<210> SEQ ID NO 53
<211> LENGTH: 22
<212> TYPE: DNA
<213> ORGANISM: Artificial Sequence
<220> FEATURE:
<223> OTHER INFORMATION: the specific primer for amplifying PIC gene
      into full-length

<400> SEQUENCE: 53
atgtctgttg ccttgttatg gg                                                  22

<210> SEQ ID NO 54
<211> LENGTH: 20
<212> TYPE: DNA
<213> ORGANISM: Artificial Sequence
<220> FEATURE:
<223> OTHER INFORMATION: the specific primer for amplifying PIC gene
      into full-length

<400> SEQUENCE: 54
tcaaatcaga tcctccagca                                                     20
```

```
<210> SEQ ID NO 55
<211> LENGTH: 18
<212> TYPE: DNA
<213> ORGANISM: Oryza sativa

<400> SEQUENCE: 55
ccgagcccag gttcaagt                                                       18

<210> SEQ ID NO 56
<211> LENGTH: 21
<212> TYPE: DNA
<213> ORGANISM: Oryza sativa

<400> SEQUENCE: 56
aagaggattc cgccacatta t                                                   21

<210> SEQ ID NO 57
<211> LENGTH: 8513
<212> TYPE: DNA
<213> ORGANISM: Artificial Sequence
<220> FEATURE:
<223> OTHER INFORMATION: pMJ-103 vector(right border to left border)
<220> FEATURE:
<221> NAME/KEY: misc_feature
<222> LOCATION: (1)..(25)
<223> OTHER INFORMATION: right border
<220> FEATURE:
<221> NAME/KEY: misc_feature
<222> LOCATION: (200)..(1569)
<223> OTHER INFORMATION: MAR(+)
<220> FEATURE:
<221> NAME/KEY: misc_feature
<222> LOCATION: (1685)..(2609)
<223> OTHER INFORMATION: Glb promoter
<220> FEATURE:
<221> NAME/KEY: misc_feature
<222> LOCATION: (2621)..(2745)
<223> OTHER INFORMATION: attR1
<220> FEATURE:
<221> NAME/KEY: misc_feature
<222> LOCATION: (2746)..(4200)
<223> OTHER INFORMATION: CmR ccdB(+)
<220> FEATURE:
<221> NAME/KEY: misc_feature
<222> LOCATION: (4201)..(4328)
<223> OTHER INFORMATION: attR2
<220> FEATURE:
<221> NAME/KEY: misc_feature
<222> LOCATION: (4370)..(4775)
<223> OTHER INFORMATION: PinII
<220> FEATURE:
<221> NAME/KEY: misc_feature
<222> LOCATION: (5326)..(6160)
<223> OTHER INFORMATION: 35S promoter
<220> FEATURE:
<221> NAME/KEY: misc_feature
<222> LOCATION: (6183)..(6734)
<223> OTHER INFORMATION: Bar gene(+)
<220> FEATURE:
<221> NAME/KEY: misc_feature
<222> LOCATION: (6752)..(7005)
<223> OTHER INFORMATION: Nos terminator
<220> FEATURE:
<221> NAME/KEY: misc_feature
<222> LOCATION: (7056)..(8424)
<223> OTHER INFORMATION: MAR(-)
<220> FEATURE:
<221> NAME/KEY: misc_feature
<222> LOCATION: (8489)..(8513)
<223> OTHER INFORMATION: left border

<400> SEQUENCE: 57
gtttacccgc caatatatcc tgtcaaacac tgatagttta aactgaaggc gggaaacgac          60
```

```
aatctgatca tgagcggaga attaagggag tcacgttatg accccccgccg atgacgcggg      120 acaagccgtt ttacgtttgg aactgacaga accgcaacgt tgaaggagcc actcagcaag      180
cttgcatgcc tcgacgtgac tgacggcttc ctatgcgtgc tcaggaaacg gcagttgggc      240
actgcactgc ccggtgatgg tgccacggtg gctcctgccg ccttctttga tattcactct      300
gttgtatttc atctcttctt gccgatgaaa ggatataaca gtctgtgagg aaatacttgg      360
tatttcttct gatcagcgtt tttataagta atgttgaata ttggataaag cctgtgtgtc      420
ctttgtcttg ggagacaaag cccacagcag gtggtggttg gggtggtggc agctcagtga      480
caggagaggt ttttttgcct gttttttttt tttttttttt ttttaagtaa ggtgttcttt      540
tttcttagta aattttctac tggactgtat gttttgacag gtcagaaaca tttcttcaaa      600
agaagaacct tttggaaact gtacagccct tttctttcat tccctttttg ctttctgtgc      660
caatgccttt ggttctgatt gcattatgga aaacgttgat cggaacttga ggttttttatt     720 tatagtgtgg cttgaaagct tggatagctg ttgttacacg agataccttta ttaagtttag    780 gccagcttga tgctttattt tttccctttg aagtagtgag cgttctctgg tttttttcct      840 ttgaaactg tgaggcttag attttttctaa tgggattttt tacctgatga tctagttgca      900
tacccaaatg cttgtaaatg ttttcctagt taacatgttg ataacttcgg atttacatgt      960
tgtatatact tgtcatctgt gttctagta aaaatatatg gcatttatag aaatacgtaa      1020
ttcctgattt cctttttttt ttatctctat gctctgtgtg tacaggtcaa acagacttca     1080
ctcctatttt tatttataga atttataatg cagtctgtcg ttggttcttg tgttgtaagg     1140
atacagcctt aaatttccta gagcgatgct cagtaaggcg ggttgtcaca tgggttcaaa     1200
tgtaaaacgg gcacgtttgg ctgctgcctt cccgagatcc aggacactaa actgctactg     1260
cactgaggta taaatcgctt cagatcccag ggaagtgtag atccacgtgc atattcttaa     1320
agaagaatga atactttcta aaatattttg gcataggaag caagctgcat ggatttgttt     1380
gggacttaaa ttattttggt aacggagtgc ataggtttta aacacagttg cagcatgcta     1440
acgagtcaca gcatttatgc agaagtgatg cctgttgcag ctgtttacgg cactgccttg     1500
cagtgagcat tgcagatagg ggtggggtgc tttgtgtcgt gttcccacac gctgccacac     1560
agccacctcc tcgaggtcga cggtatcgat aagcttgata tcgaattcct gcaggtcgac     1620
tctagagtcc gcctggaggg aggagagggg agagatggtg agagaggagg aagaagagga     1680
ggggtgacaa tgatatgtgg ggccatgtgg gccccaccat ttttttaattc attcttttgt    1740 tgaaactgac atgtgggtcc catgagattt attattttttc ggatcgaatt gccacgtaag    1800
cgctacgtca atgctacgtc agatgaagac cgagtcaaat tagccacgta agcgccacgt    1860
cagccaaaac caccatccaa accgccgagg gacctcatct gcactggttt tgatagttga    1920
gggacccgtt gtatcggtt tttcgattga aggacgaaaa tcaaatttgt tgacaagtta    1980 agggaccta aatgaactta ttccatttca aaatattctg tgagccatat atccgtgggc    2040
ttccaatcct cctcaaatta aagggccttt ttaaaataga taattgcctt ctttcagtca    2100
cccataaaag tacaaaacta ctaccaacaa gcaaacatgcg cagttacaca catttttctgc    2160 acatttccac cacgtcacaa agagctaaga gttatcccta ggacaatctc attagtgtag    2220
atacatccat taatctttta tcagaggcaa acgtaaagcc gctctttatg acaaaaatag    2280
gtgacacaaa agtgttatct gccacataca taacttcaga aattacccaa caccaagaga    2340
aaaataaaaa aaaatctttt tgcaagctcc aaatcttgga aaccttttc actctttgca     2400 gcattgtact cttgctcttt ttccaaccga tccatgtcac cctcaagctt ctacttgatc    2460
```

```
tacacgaagc tcaccgtgca cacaaccatg gccacaaaaa ccctataaaa ccccatccga   2520
tcgccatcat ctcatcatca gttcatcacc aacaaacaaa agaggaaaaa aaacatatac   2580
acttctagtg attgtctgat tgatcatcag gatccccatc acaagtttgt acaaaaaagc   2640
tgaacgagaa acgtaaaatg atataaatat caatatatta aattagattt tgcataaaaa   2700
acagactaca taatactgta aaacacaaca tatccagtca ctatggcggc cgcattaggc   2760
accccaggct ttacacttta tgcttccggc tcgtataatg tgtggatttt gagttaggat   2820
ccgtcgagat tttcaggagc taaggaagct aaaatggaga aaaaaatcac tggatatacc   2880
accgttgata tatcccaatg gcatcgtaaa gaacattttg aggcatttca gtcagttgct   2940
caatgtacct ataaccagac cgttcagctg gatattacgg cctttttaaa gaccgtaaag   3000
aaaaataagc acaagtttta tccggccttt attcacattc ttgcccgcct gatgaatgct   3060
catccggaat tccgtatggc aatgaaagac ggtgagctgg tgatatggga tagtgttcac   3120
ccttgttaca ccgttttcca tgagcaaact gaaacgtttt catcgctctg gagtgaatac   3180
cacgacgatt tccggcagtt tctacacata tattcgcaag atgtggcgtg ttacggtgaa   3240
aacctggcct atttccctaa agggtttatt gagaatatgt ttttcgtctc agccaatccc   3300
tgggtgagtt tcaccagttt tgatttaaac gtggccaata tggacaactt cttcgccccc   3360
gttttcacca tgggcaaata ttatacgcaa ggcgacaagg tgctgatgcc gctggcgatt   3420
caggttcatc atgccgtttg tgatggcttc catgtcggca gaatgcttaa tgaattacaa   3480
cagtactgcg atgagtggca gggcggggcg taaacgcgtg gatccggctt actaaaagcc   3540
agataacagt atgcgtattt gcgcgctgat ttttgcggta taagaatata tactgatatg   3600
tatacccgaa gtatgtcaaa aagaggtatg ctatgaagca gcgtattaca gtgacagttg   3660
acagcgacag ctatcagttg ctcaaggcat atatgatgtc aatatctccg gtctggtaag   3720
cacaaccatg cagaatgaag cccgtcgtct gcgtgccgaa cgctggaaag cggaaaatca   3780
ggaagggatg gctgaggtcg cccggtttat tgaaatgaac ggctcttttg ctgacgagaa   3840
caggggctgg tgaaatgcag tttaaggttt acacctataa aagagagagc cgttatcgtc   3900
tgtttgtgga tgtacagagt gatattattg acacgcccgg gcgacggatg gtgatccccc   3960
tggccagtgc acgtctgctg tcagataaag tctcccgtga actttacccg gtggtgcata   4020
tcggggatga agctggcgc atgatgacca ccgatatggc cagtgtgccg gtctccgtta   4080
tcggggaaga agtggctgat ctcagccacc gcgaaaatga catcaaaaac gccattaacc   4140
tgatgttctg gggaatataa atgtcaggct cccttataca cagccagtct gcaggtcgac   4200
catagtgact ggatatgttg tgttttacag tattatgtag tctgttttttt atgcaaaatc   4260 taatttaata tattgatatt tatatcattt tacgtttctc gttcagcttt cttgtacaaa   4320
gtggtgatgg ggatccacta gttctagagc ggccgctcta gctagagtca ccctgcaatg   4380
tgaccctaga cttgtccatc ttctggattg gccaacttaa ttaatgtatg aaataaaagg   4440
atgcacacat agtgacatgc taatcactat aatgtgggca tcaaagttgt gtgttatgtg   4500
taattactaa ttatctgaat aagagaaaga gatcatccat atttcttatc ctaaatgaat   4560
gtcacgtgtc tttataattc tttgatgaac cagatgcatt ttattaacca attccatata   4620
catataaata ttaatcatat ataattaata tcaattggg tagcaaaaca aatctagtct   4680
aggtgtgttt tgctaattat tggggatag tgcaaaaga aatctacgtt ctcaataatt   4740
cagatagaaa acttaataaa gtgagataat ttacatagat tgcttttatc ctttgatata   4800
tgtgaaacca tgcatgatat aaggaaaata gatagagaaa taatttttta catcgttgaa   4860
```

```
tatgtaaaca atttaattca agaagctagg aatataaata ttgaggagtt tatgattatt    4920
attattattt tgatgttcaa tgaagttttt tttaatttca tatgaagtat acaaaaattc    4980
ttcatagatt tttgtttcta tgccgtagtt atctttaata tatttgtggt tgaagaaatt    5040
tattgctaga aacgaatgga ttgtcaattt ttttttaaag caaatatata tgaaattata    5100
ctgtatatta ttttagtcat gattaaaatg tggccttaat tgaatcatct ttctcattca    5160 tttttttcaaa agcatatcag gatgattgat atttatctat tttaaaaatt aatttaaggg    5220
ttcaaattaa atttaactta aaagtgtcct aaccgtagtt aaaggtttac tttaaaaaaa    5280
tactatgaaa aatctaatct tctatgaatc gacctgcagg tccccagatt agccttttca    5340
atttcagaaa gaatgctaac ccacagatgg ttagagaggc ttacgcagca ggtctcatca    5400
agacgatcta cccgagcaat aatctccagg aaatcaaata ccttcccaag aaggttaaag    5460
atgcagtcaa aagattcagg actaactgca tcaagaacac agagaaagat atatttctca    5520
agatcagaag tactattcca gtatggacga ttcaaggctt gcttcacaaa ccaaggcaag    5580
taatagagat tggagtctct aaaaaggtag ttcccactga atcaaaggcc atggagtcaa    5640
agattcaaat agaggaccta acagaactcg ccgtaaagac tggcgaacag ttcatacaga    5700
gtctcttacg actcaatgac aagaagaaaa tcttcgtcaa catggtggag cacgacacac    5760
ttgtctactc caaaaatatc aaagatacag tctcagaaga ccaaagggca attgagactt    5820
ttcaacaaag ggtaatatcc ggaaacctcc tcggattcca ttgcccagct atctgtcact    5880
ttattgtgaa gatagtggaa aaggaagtg gctcctacaa atgccatcat tgcgataaag    5940
gaaaggccat cgttgaagat gcctctgccg acagtggtcc caaagatgga cccccaccca    6000
cgaggagcat cgtggaaaaa gaagacgttc caaccacgtc ttcaaagcaa gtggattgat    6060
gtgatatctc cactgacgta agggatgacg cacaatccca ctatccttcg caagacccTT    6120
cctctatata aggaagttca tttcatttgg agagaacacg ggggactcta gggggatcta    6180
ccatgagccc agaacgacgc ccggccgaca tccgccgtgc caccgaggcg gacatgccgg    6240
cggtctgcac catcgtcaac cactacatcg agacaagcac ggtcaacttc cgtaccgagc    6300
cgcaggaacc gcaggagtgg acggacgacc tcgtccgtct gcgggagcgc tatccctggc    6360
tcgtcgccga ggtggacggc gaggtcgccg gcatcgccta cgcgggcccc tggaaggcac    6420
gcaacgccta cgactggacg gccgagtcga ccgtgtacgt ctccccccgc caccagcgga    6480
cgggactggg ctccacgctc tacacccacc tgctgaagtc cctggaggca cagggcttca    6540
agagcgtggt cgctgtcatc gggctgccca acgacccgag cgtgcgcatg cacgaggcgc    6600
tcggatatgc ccccgcggc atgctgcggg cggccggctt caagcacggg aactggcatg    6660
acgtgggttt ctggcagctg gacttcagcc tgccggtacc gccccgtccg gtcctgcccg    6720
tcaccgagat ctgatgaccc cgaatttccc cgatcgttca acatttggc aataaagttt    6780 cttaagattg aatcctgttg ccggtcttgc gatgattatc atataatttc tgttgaatta    6840
cgttaagcat gtaataatta acatgtaatg catgacgtta tttatgagat gggtttttat    6900
gattagagtc ccgcaattat acatttaata cgcgatagaa aacaaaatat agcgcgcaaa    6960
ctaggataaa ttatcgcgcg cggtgtcatc tatgttacta gatcgggaat tcgatatcaa    7020
gctgaggggg ggcccggtac cgagctccac cgcgggaggt ggctgtgtgg cagcgtgtgg    7080
gaacacgaca caaagcaccc caccccctatc tgcaatgccc actgcaaggc agtgccgtaa    7140
acagctgcaa caggcatcac ttctgcataa atgctgtgac tctttatcat gctgcaactg    7200
tgtttaaaac ctatgcactc cgttaccaaa ataatttaag tcccaaacaa atccatgcag    7260
```

```
cttgcttcct atgccaaaat attttagaaa gtattcattc ttctttaaga atatgcacgt    7320
ggatctacac ttccctggga tctgaagcga tttatacctc agtgcagaag cagtttagtg    7380
tcctggatct cgggaaggca gcagccaaac gtgcccgttt tacatttgaa cccatgtgac    7440
aacccgcctt actgagcatc gctctaggaa atttaaggct gtatccttac aacacaagaa    7500
ccaacgacag actgcatata aaattctata aataaaaata ggagtgaagt ctgtttgacc    7560
tgtacacaca gagcatagag ataaaaaaaa aggaaatcag gaattacgta tttctataaa    7620
tgccatatat ttttactaga aacacagatg acaagtatat acaacatgta aatccgaagt    7680
tatcaacatg ttaactagga aaacatttac aagcatttgg gtatgcaact agatcatcag    7740
gtaaaaaatc ccattagaaa aatctaagcc tcaccagttt caaaggaaaa aaaccagaga    7800
acgctcacta cttcaaaggg aaaaaataaa gcatcaagct ggcctaaact taataaggta    7860
tctcgtgtaa caacagctat ccaagctttc aagccacact ataaataaaa acctcaagtt    7920
ccgatcaacg ttttccataa tgcaatcaga accaaaggca ttggcacaga aagcaaaaag    7980
ggaatgaaag aaaagggctg tacagtttcc aaaaggttct tcttttgaag aaatgtttct    8040
gacctgtcaa aacatacagt ccagtagaaa tttattaag aaaaaagaac accttactta     8100
aaaaaaaaaa caacaaaaaa aacaggcaaa aaaacctctc ctgtcactga gctgccacca    8160 ncccaacca ccacctgctg tgggctttgt ctcccaagac aaaggacaca cagccttatc      8220
caatattcaa cattacttat aaaaacgctg atcagaagaa ataccaagta tttcctcaca    8280
gactgttata tcctttcatc ggcaagaaga gatgaaatac aacagagtga atatcaaaga    8340
aggcggcagg agccaccgtg gcaccatcac cgggcagtgc agtgcccaac tgccgtttcc    8400
tgagcacgca taggaagccg tcaggagctc gaattcagta cattaaaaac gtccgcaatg    8460
tgttattaag ttgtctaagc gtcaatttgt ttacaccaca atatatcctg cca           8513
```

FUSION POLYNUCLEOTIDE FOR BIOSYNTHESIS OF BETA-CAROTENE USING BICISTRONIC GENE EXPRESSION AND METHOD FOR PRODUCING BETA-CAROTENE USING THE SAME

CROSS-REFERENCES TO RELATED APPLICATIONS

This application is a U.S. national phase application, pursuant to 35 U.S.C. §371 of PCT/KR2008/005086, filed Aug. 29, 2008, designating the United States, which claims priority to Korean Application No. 10-2007-0087608, filed Aug. 30, 2007; which claims priority to Korean Application No. 10-2008-0010138, filed Jan. 31, 2008. The entire contents of the aforementioned patent applications are incorporated herein by this reference.

TECHNICAL FIELD

The present invention relates to a fusion polynucleotide for biosynthesis of beta-carotene using a co-expression of multi-cistronic genes and a method for producing beta-carotene using the same. More particularly, it relates to a fusion polynucleotide encoding phytoene synthase, connective sequences of FMDV-derived 2A sequence or internal ribosome entry site (IRES) and carotene desaturase and a method for producing beta-carotene using the same.

BACKGROUND ART

As molecular biological techniques are advancing, various genetic engineering methods have been developed in order to produce useful metabolic substance and to modify the substance in an effective form. In practice, a lot of studies on plant metabolic engineering and plant molecular farming have been accomplished. The plant metabolic engineering is to utilize a plant for mediator and the plant molecular farming is to produce high value-added non-plant edible vaccines from non-plant and recombinant proteins for medical use etc from plant. However, there are various technical difficulties and research outcomes are not successful yet.

Especially in order to regulate a metabolic process, it may be useful to express several genes coincidently under a condition. Presently, model researches using reporter genes in tobacco were just attempted in this field. In contrast to prokaryotes, it is difficult to regulate multi-cistronic genes expression in eukaryotes such as plant and animal. The eukaryote has a feature to express only one gene from one promoter by a mono-cistronic mRNA mechanism.

In general, *Agrobacterium* is applied to transform a plant by inserting a T-DNA. In this case, (1) introduction of multi-cassettes in one T-DNA; (2) co-transformation of *Agrobacterium*; (3) sexual crossing between transformants; and (4) insertion of multi-cistronic genes into a cassette; are often conducted in order to introduce and express multi-cistronic genes coincidently.

Precisely, the method for introducing the multi-cassettes in one T-DNA is popularly used. Unfortunately, it is hard to express more than two target genes excluding a selective marker gene with one T-DNA vector, because the total number of cassettes for transformation is limited to 3 or 4. Furthermore, when conducting the *Agrobacterium* mediated co-transformation, each T-DNA should have a different selective marker in order to select transformants. In this case, the selective marker may be a limiting factor to block the plant transformation. Therefore, this procedure is disadvantageous to restrict applicable fields.

The method for stacking genes by using a sexual crossing between transformants collects useful traits of each individual into a plant. But, this procedure needs to consume a long time period and is hard to control a result exactly.

Besides, the method for introducing multi-cistronic genes into a cassette has been tried to precede metabolic engineering studies and to obtain complex resistance traits against stress or diseases. In this process, the eukaryotic mechanism of protein expressions is applied so that specific recognition sites of a eukaryote are introduced at between target genes.

DISCLOSURE

Technical Problem

The present inventors have tried to develop genetically engineered plants. We have manufactured fusion polynucleotides that can express biologically active beta-carotenes by using a multi-cistronic gene expression technique and recombinant vectors containing the fusion gene. By using the fusion polynucleotide and the recombinant vector, we have also developed plant transformants that produces nutritional beta-carotenes in a rice plant, although this cannot naturally express carotenoids at all, and completed the invention successfully.

Therefore, the present invention has been made in view of the above problems, and it is an object of the present invention to provide fusion polynucleotides for the biosynthesis of beta-carotene and uses of the same.

Technical Solution

In order to attain an object of the present invention, the present invention provides a fusion polynucleotide expressing phytoene synthase and carotene desaturase to biosynthesize.

In order to attain another object of the present invention, the present invention provides a recombinant vector containing the fusion polynucleotide for plant transformation.

In order to attain another object of the present invention, the present invention provides a cell transformed with the recombinant vector.

In order to attain another object of the present invention, the present invention provides a plant cell or a transformant transformed with the recombinant vector to biosynthesize beta-carotene.

In order to attain another object of the present invention, the present invention provides a method for producing beta-carotene by using the plant cell or the transformant transformed with the recombinant vector to biosynthesize beta-carotene.

Hereinafter, the present invention will be explained more clearly.

In accordance with an aspect of the present invention, the above and other objects can be accomplished by the provision of fusion polynucleotides encoding phytoene synthase, connective sequences of FMDV-derived 2A sequence or internal ribosome entry site (IRES) and carotene desaturase.

Preferably, the fusion polynucleotide of the present invention can be DNA or RNA of SEQ ID NO: 1 or SEQ ID NO: 42. When the polynucleotide is RNA, thymine (T) can be replaced by uracil (U). The polynucleotide of the present invention can be manufactured by any chemical synthetic process disclosed in prior arts.

In accordance with another aspect of the present invention, there is provided recombinant vectors containing the fusion polynucleotide comprising polynucleotide encoding phytoene synthase, connective sequences of FMDV-derived 2A sequence or internal ribosome entry site (IRES) and polynucleotide encoding carotene desaturase.

In general, beta-carotene is synthesized by the process described in FIG. 2. Within a plant, the basic synthetic pathway of carotenoids is comprised of following steps: 2 molecules of GGPP (geranylgeranyl pyrophosphate) are polymerized to phytoene composed of 40 carbons (three conjugated double bonds) by phytoene synthase (PSY); prepared to ζ-carotene (seven conjugated double bonds) after two-step desaturation by phytoene desaturase (PDS); then reacted by using ζ-carotene desaturase (ZDS) through additional two-step desaturation; and finally prepared to lycopene (eleven conjugated double bonds) via neurosporene (nine conjugated double bonds). Lycopene is an end product of noncircular carotenoids and is converted to two kinds of circular carotenes. One carotene is a β-carotene that is synthesized from γ-carotene through two-step reaction using lycopene-β-cyclase (β-LCY). The other carotene is an α-carotene that is synthesized from γ-carotene and β-carotene, respectively, through cooperative reaction using lycopene-ε-cyclase (ε-LCY) and β-LCY. But in a rice plant, because the phytoene synthase (PSY), an initial enzyme of carotenoid biosynthesis, is not expressed, any kind of carotenoid is not produced at all. Therefore, the present inventors have constructed recombinant vectors containing a promoter, and a polynucleotide encoding phytoene synthase, connective sequences of FMDV-derived 2A sequence or internal ribosome entry site (IRES) and a polynucleotide encoding carotene desaturase operably linked the promoter. Then, we have expressed the enzymes to produce beta-carotene from a rice plant in a large scale using the recombinant vector.

The phytoene synthase is a biosynthetic enzyme that polymerizes 2 molecules of GGPP (geranylgeranyl pyrophosphate) to produce phytoenes. In the present invention, any kind of phytoene synthase enzyme or any kind of polynucleotide encoding the same can be used if disclosed. Preferably, they can be derived from pepper, tomato, *Arabidopsis*, potato and the like and more preferably, the polynucleotide of phytoene synthase can be the nucleotide sequence of SEQ ID NO: 5 or SEQ ID NO: 6.

The FMDV (foot and mouth disease virus)-derived 2A sequence is self-processed through an intra-ribosomal "skip" mechanism during translation [Donnelly et al., 1997, *J. Gen. Virol.*, 78, 13-21; Ryan et al., 1991, *J. Gen. Virol.*, 72, 2727-2732]. Preferably, the FMDV-derived 2A sequence can contain the amino acid sequence of SEQ ID NO: 2 and the polynucleotide encoding the FMDV-derived 2A sequence can contain the nucleotide sequence of SEQ ID NO: 3. The amino acid sequence and the nucleotide sequence of the present invention are optimized for rice plant.

The internal ribosome entry site (IRES) is a nucleotide sequence that initiates a translation in the middle of mRNA. Preferably, the IRES can have the nucleotide sequence of SEQ ID NO: 31 and corresponds to 150 bp-upstream of coat protein derived from CrTMV (crucifer-infecting tobamovirus).

The carotene desaturase (CrtI) is a desaturase derived from *Erwinia uredovora* or *Pantoea ananatis* and plays both roles of two kinds of desaturases, PDS and ZDS to convert phytoene to lycopene. In the present invention, any kind of carotene desaturase enzyme or polynucleotide encoding the same disclosed in prior arts can be used. Preferably, the carotene desaturase can have the amino acid sequence of SEQ ID NO: 7 and the polynucleotide can have the nucleotide sequence of SEQ ID NO: 8.

In the present invention, the fusion protein comprising phytoene synthase, connective sequences of FMDV-derived 2A sequence or internal ribosome entry site and carotene desaturase can include functional equivalents of the protein. This functional equivalent is defined as a polypeptide that has a substantially similar physiological activity to phytoene synthase, connective sequences of FMDV-derived 2A sequence or internal ribosome entry site and carotene desaturase. The "substantially similar physiological activity" is a biological activity: producing phytoene by polymerizing two molecules of GGPP (geranylgeranyl pyrophosphate); self-processing through a non-proteolytic mechanism; and entering internal ribosome and converting phytoene to lycopene by PDS and ZDS.

Preferably, the functional equivalent can be a polypeptide having any sequence homology (identity) with the amino acid sequences of SEQ ID NO: 5; SEQ ID NO: 2 or SEQ ID NO: 31; SEQ ID NO: 7 corresponding to phytoene synthase, connective sequences of FMDV-derived 2A sequence or internal ribosome entry site and carotene desaturase, respectively. Preferably, the sequence homology is at least 70%, more preferably at least 80% and most preferably at least 90%. Precisely, the functional equivalent can includes a polypeptide having 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% of the sequence homology.

The functional equivalent can be prepared by using a partial addition, substitution or deletion of amino acid sequences from phytoene synthase, connective sequences of FMDV-derived 2A sequence or internal ribosome entry site and carotene desaturase. Preferably, the substitution of amino acids is a conservative substitution. For example, the conservative substitution of amino acids can be accomplished in aliphatic amino acids (Gly, Ala, Pro), hydrophobic amino acids (Ile, Leu, Val), aromatic amino acids (Phe, Tyr, Trp), acidic amino acids (Asp, Glu), basic amino acids (His, Lys, Arg, Gln, Asn) and sulfur-containing amino acids (Cys, Met). In addition, the deletion of amino acids can include a modification with partial deletion in the amino acid sequence of phytoene synthase, connective sequences of FMDV-derived 2A sequence or internal ribosome entry site and carotene desaturase. Preferably, the deletion of amino acids and the substitution are situated at a region unaffected directly. Besides, the addition of amino acids can include a modification of attaching more than one amino acid in both ends or within the amino acid sequence of phytoene synthase, connective sequences of FMDV-derived 2A sequence or internal ribosome entry site and carotene desaturase. The functional equivalent also includes a polypeptide derivative that maintains a backbone and physiological activities, but partially modified in the chemical structure. For example, the functional equivalent includes a structural modification for changing its stability, storage, volatility, solubility or purity.

In the present invention, the recombinant vectors containing the fusion polynucleotide that encode phytoene synthase, connective sequences of FMDV-derived 2A sequence or internal ribosome entry site (IRES) and carotene desaturase, can be constructed by using any basic vector for plant transformation disclosed in prior arts. Preferably, binary vectors or cointegration vectors can be used. Various kinds of binary vectors are widely used for plant transformation and almost all binary vectors are commercially available. They can be obtained from international organizations and research institutes of universities such as CAMBIA (The Center for the Application of Molecular Biology to International Agriculture, GPO Box 3200, Canberra ACT2601, Australia). The basic structure of binary vectors is originated from Ti plasmid and modified at a left and a right border with exogenous genes, promoters and terminators etc.

In the present invention, the recombinant vectors can adopt any promoter disclosed in prior arts, if functional in a plant. The fusion polynucleotide that encodes phytoene synthase, connective sequences of FMDV-derived 2A sequence or internal ribosome entry site (IRES) and carotene desaturase is operatively linked to the downstream of promoter. The promoter is a DNA sequence that regulates a gene expression at its downstream in a specific host cell. The operative linkage is a connection affected by each other to function or express the same, when nucleic acids are combined. The recombinant vectors can also contain any operator sequence for transcription regulation, proper sequence encoding an mRNA ribosome binding site and terminator of transcription and translation.

Preferably, the promoter can be selected from a group comprising rice endosperm-specific globulin (Glb) promoter, glutelin (GT, Glt or Glu) promoter, corn ubiquitin (Ubi) promoter, Cauliflower Mosaic Virus (CaMV) 35S promoter, figwort mosaic virus 35S promoter, sugarcane bacilliform virus promoter, Commelina yellow mottle virus promoter, light-induced promoter derived from ribulose-1,5-bis-phosphate carboxylase subunit (ssRUBISCO), rice cytosolic tri-o-phosphate isomerase (TPI) promoter, adenine phosphoribosyl transferase (APRT) promoter derived from *Arabidopsis*, rice actin1 gene promoter, mannopin synthase promoter and octopin synthase promoter. More preferably, it can be rice endosperm-specific globulin (Glb) promoter.

Preferably, the selective marker gene can be adopted from a group comprising antibiotic resistance gene, herbicide resistance gene, metabolism-related gene, luminescence gene, green fluorescence protein (GFP) gene, β-glucuronidase (GUS) gene, β-galactosidase (GAL) gene and the like, but not limited. More preferably, it can be selected from a group comprising herbicide resistant Bar gene, neomycin phosphotransferase II (NPT II) gene, hygromycin phosphotransferase gene, phosphinothricine acetyltransferase gene or dehydrofolate reductase gene and the like and most preferably, it can be herbicide resistant Bar gene.

Preferably, the recombinant vectors for plant transformation of the present invention can be the pGlb-PAC vector illustrated in FIG. 1 or the pGlb-PIC vector illustrated in FIG. 9. In detail, the pGlb-PAC vector is constructed by using the pMJ-103 vector (from right border to left border is represented by SEQ ID: 57) for backbone wherein attB1 sequence, polynucleotide encoding pepper phytoene synthase, connective sequences of FMDV-derived 2A sequence, polynucleotide encoding bacterial carotene desaturase and attB2 sequence are connected in serial order between the rice endosperm-specific globulin (Glb) promoter and the terminator of potato protease inhibitor II (Pin II). Further, the pGlb-PIC vector is constructed from the pGlb-PAC vector by exchanging the FMDV-derived 2A sequence for an internal ribosome entry site. In this case, the pMJ-103 vector has been made by using the pSB11 vector (Genbank Acession No. AB027256) for backbone, a super-binary plasmid containing spectinomycin resistant gene. The pMJ-103 vector is a gateway vehicle integrating rice endosperm-specific globulin (Glb) promoter and terminator of potato protease inhibitor II (Pin II) and contains herbicide resistant Bar gene at the downstream region of 35S promoter for plant selective marker.

The standard recombinant DNA and molecular cloning techniques of above-mentioned are well known in the art and are described in the followed references. (Sambrook, J., Fritsch, E. F. and Maniatis, T., Molecular Cloning: A Laboratory Manual, 2nd ed., Cold Spring Harbor Laboratory: Cold Spring Harbor, N.Y. 1989; by Silhavy, T. J., Bennan, M. L. and Enquist, L. W., Experiments with Gene Fusions, Cold Spring Harbor Laboratory: Cold Spring Harbor, N.Y., 1984; and by Ausubel, F. M. et al., Current Protocols in Molecular Biology, published by Greene Publishing Assoc. and Wiley-interscience, 1987).

Meanwhile, in an embodiment of the present invention, a recombinant vector of the present invention was transformed into *Agrobacterium tumefacience* LBA4404 and the gene of the present invention was introduced into the plant cell by the transformed *Agrobacterium*.

Accordingly, the present invention provides a cell which is transformed with vector for a plant cell transfomation of the present invention. The transformed cell may, but not limited thereto, prokaryotic host cell such as *Agrobacterium* spp., *Escherichia coli*, *Bacillus subtilis*, *Streptomyces*, *Pseudomonas*, *Proteus mirabilis* or *Staphylococcus*, lower eukaryotic cell such as fungi (for example, *Aspergillus*) and yeast (for example, *Pichia pastoris*, *Saccharomyces cerevisiae*, *Schizosaccharomyces*, *Neurospora crassa*), and a higher eukaryote originated cell which is comparing an insect cell, a plant cell, and mammalian cell, and preferably *Agrobacterium tumefacience* or *Agrobacterium rhizogenes*.

In addition, the present invention provides a transformed plant cell which is introduced the said vector, and produce beta-carotene.

Transformed plant cell may prepared by the plant transforming method disclosed in prior arts. For example, but not limited thereto, transformation by using *Agrobacterium* spp., particle gun bombardment, Silicon carbide whiskers, sonication, electroporation and precipitation by PEG(poly ethylene glycol) may be used. Preferably, *Agrobacterium*-midiated transformation may be used (Horsch et al., Science 227:1229-1231, 1985). For example, *Agrobacterium*-midiated transformation for rice is disclosed in prior arts (An et al., EMBO J., 4:227-288, 1985).

The plant cell of the present invention can be cultivated according to any conventional procedure and include broth-cultured cell, callus, cultured protoplast and further, plant tissue or plant after being differentiated. Precisely, the plant transformed with the recombinant vector can be induced to a callus, rooted and refined on soil by using standard techniques disclosed in prior arts so as to be re-differentiated into a plant. The resulting plant can be produced by both asexual and sexual procedure. The asexual method includes cuttage, graft and the like and the sexual method includes seeding.

The plant cell culture is conducted under a germ-free condition after being separated from a part of mother plant and then, proliferated. This process can be accomplished by any process disclosed in prior arts and includes broth culture of tissue fragment, callus culture of tissue fragment, protoplast culture and the like. This culture condition and procedure can be determined by those skilled in the arts.

The differentiation of the plant cell is performed under a proper condition to induce differentiation of cultured callus or protoplast. The resulting callus and protoplast can generate a plant tissue or plant. This condition and procedure of differentiation can be determined by those skilled in the arts.

In accordance with another aspect of the present invention, there is provided recombinant plants or mushrooms transformed with the recombinant vectors to produce beta-carotene.

The plant described above can include whole plant, a part of plant, callus, plant tissue, plant cell and plant seed. The plant of the present invention can include mono-cotyledon or di-cotyledon plant. The mono-cotyledon plant is not limited, but preferably can be rice plant, wheat, barley, bamboo shoot, corn, taro, asparagus, onion, garlic, welsh onion, scallion, wild rocambole, yam and ginger. The di-cotyledon plant is not limited, but preferably can be *Arabidopsis*, eggplant, tobacco, pepper, tomato, burdock, crown daisy, lettuce, bellflower, spinach, spinach beet, sweet potato, salary, carrot, dropwort, parsley, white cabbage, cabbage, radish, water melon, melon, cucumber, pumpkin, gourd, strawberry, soy bean, mung bean, kidney bean, bird's-foot trefoil, potato, duckweed, green perilla, pigeon pea, narcissus, marigold and green bean.

In accordance with another aspect of the present invention, there is provided a method for producing beta-carotene which comprises following steps: (a) introducing a recombinant vector containing the fusion polynucleotide of the present invention into a cell; (b) culturing the cell or a plant differentiated from the cell; and (c) separating beta-carotene from the cell or the plant after being cultured.

The recombinant vectors and the cell transformation are clearly described above. The cell transformed with the recombinant vector is differentiated to an intact cell or cell group such as callus. Then, it is cultured or cultivated to express phytoene synthase gene and carotene desaturase gene integrated in the recombinant vector. The beta-carotene can be purified from the cultured cell or plant by any conventional method disclosed in prior arts and preferably, by an extraction method using organic solvent.

In an embodiment of the present invention, a pepper phytoene synthase gene and a bacterial carotene desaturase gene are separated to be cloned and the nucleotide sequence encoding the FMDV-derived 2A sequence which is optimized for rice plant by using codon usage. Then, the fusion polynucleotide of the present invention is constructed.

In another embodiment of the present invention, recombinant sequences (such as attB1 and attB2) are attached to the fusion polynucleotide and inserted into the pDONR201 vector. Then, the fusion polypeptide is transformed with the pMJ-103 vector that is composed of the pSB11 vector for backbone, rice endosperm-specific globulin (Glb) promoter and potato protease inhibitor II (PinII) terminator so as to construct the pGlb-PAC vector. The pGlb-PAC vector is introduced into *Agrobacterium* for transformation.

In another embodiment of the present invention, internal ribosome entry site that is derived from CrTMV (crucifer-infecting tobamovirus) and corresponds to 150 bp-upstream of coat protein is inserted between the pepper phytoene synthase gene and the bacterial carotene desaturase gene to construct the fusion polynucleotide.

In another embodiment of the present invention, recombinant sequences (such as attB1 and attB2) are attached to the fusion polynucleotide and inserted into the pDONR201 vector. Then, the fusion polypeptide is transformed with the pMJ-103 vector that is composed of the pSB11 vector for backbone, Glb promoter and PinII terminator to construct the pGlb-PIC vector. The pGlb-PIC vector is introduced into *Agrobacterium* for transformation.

In another embodiment of the present invention, the *Agrobacterium* transformed with the pGlb-PAC vector or the pGlb-PIC vector is used to transform a rice plant. Then, the rice plant is selected to be differentiated toward an individual plant. The plant transformant is observed to appear denser yellow color with naked eyes than a control group of intact plant.

In the other embodiment of the present invention, the plant transformant was examined whether the fusion polynucleotide is introduced and whether carotenoids are synthesized, and further measured in a RNA level and protein level of expression. As a consequence, it was confirmed that the fusion polynucleotide is inserted properly into the transformant and expressed actively in RNA level and in protein level so as to produce carotenoids highly, especially beta-carotene.

Advantageous Effects

The present invention provides fusion polynucleotides expressing both phytoene synthase gene and bacterial carotene desaturase gene stably within cell transformants, recombinant vectors, recombinant cells transformed with the recombinant vectors and plant transformants. The fusion polynucleotide of the present invention can be used to regulate the biosynthetic metabolism of plant producing beta-carotene. Furthermore, it can be applied to effectively increase the content of beta-carotene, a useful metabolite.

DESCRIPTION OF DRAWINGS

The above and other features of the present invention will now be described in detail with reference to certain exemplary embodiments thereof illustrated in the accompanying drawings which are given herein below by way of illustration only, and thus are not limitative of the present invention, and wherein.

Figure 1:
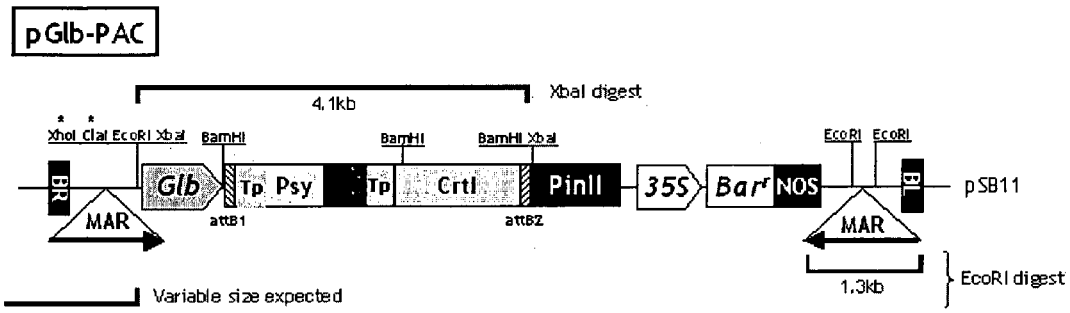
FIG. 1 is a schematic diagram of the pGlb-PAC vector (LB: left border; RB: right border; Glb: rice endosperm-specific globulin promoter; Psy: phytoene synthase gene derived from Korean pepper cv. NocKwang; st2A: 2A sequence optimized for rice plant; Tp: chroroplast target transit peptide; CrtI: bacterial carotene desaturase gene; PinII: potato protease inhibitor II terminator; P35S: CaMV 35S promoter; Bar: phosphinothricin acetyltransferase gene; NOS: nopaline synthase terminator; and MAR: matrix attachment region.)
Figure 2:
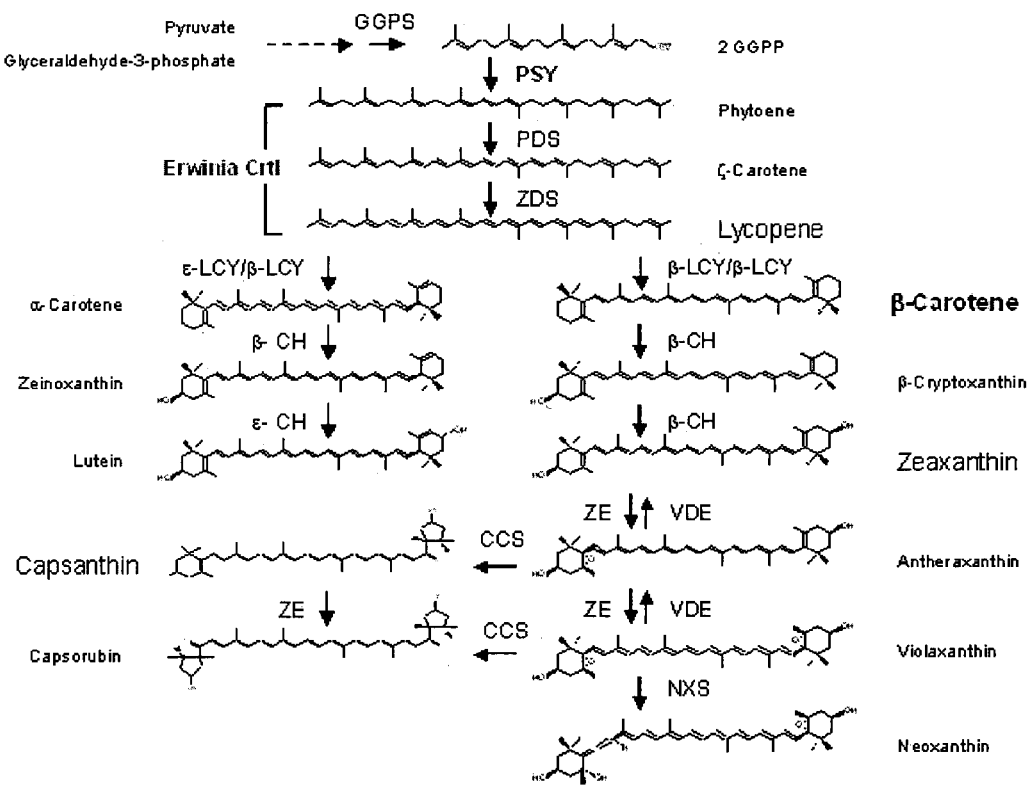
FIG. 2 is a plant metabolic process of carotenoids including beta-carotene (GGPS: geranylgeranyl pyrophosphate synthase; PSY: phytoene synthase; PDS: phytoene desaturase; ZDS: ζ-carotene desaturase; β-LCY: lycopene-β-cyclase; ε-LCY: lycopene-ε-cyclase; β-CH: β-carotene hydroxylase; ε-CH: ε-carotene hydroxylase; ZE: zeaxanthin epoxidase; VDE: violaxanthin de-epoxidase; NXS: neoxanthin synthase; CCS: capsanthin-capsorubin synthase)

It should be understood that the appended drawings are not necessarily to scale, presenting a somewhat simplified representation of various preferred features illustrative of the basic principles of the invention. The specific design features of the present invention as disclosed herein, including, for example, specific dimensions, orientations, locations, and shapes will be determined in part by the particular intended application and use environment.

BEST MODE

Hereinafter, reference will now be made in detail to various embodiments of the present invention, examples of which are illustrated in the accompanying drawings and described below. While the invention will be described in conjunction with exemplary embodiments, it will be understood that the present description is not intended to limit the invention to those exemplary embodiments. On the contrary, the invention is intended to cover not only the exemplary embodiments, but also various alternatives, modifications, equivalents and other embodiments, which may be included within the spirit and scope of the invention as defined by the appended claims.

Example 1

Synthesis of FMDV-Derived 2A Sequence (st2A Gene) Optimized for Rice Plant

FMDV (foot-and-mouse disease virus)-derived 2A sequence is known to be self-processed at a specified C-terminus of amino acids (G↓P). Within the FMDV-derived 2A sequence, the amino acid sequence of SEQ ID NO: 2 was used to design a polynucleotide optimized in a rice plant. Precisely, rice codon usage data was used to determine 60 bp of optimal nucleotide sequences. At both ends of the nucleotide sequence, 3 bp nucleotides were attached for recognition sites of restriction enzyme PstI and SmaI to design the polynucleotide of SEQ ID NO: 3 (st2A-sense ssDNA). Then, the polynucleotide of SEQ ID NO: 4 (st2A-antisense ssDNA) complementary to the polynucleotide of SEQ ID NO: 3 was also designed.

The polynucleotide of SEQ ID NO: 3 and the polynucleotide of SEQ ID NO: 4 designed above were requested to be synthesized in a commercial company. Then, these sequences were slowly annealed at from 65° C. to room temperature to be converted to double-stranded DNAs (dsDNAs). The dsDNAs were digested with restriction enzymes PstI and SmaI and ligated into the plasmid pKS+vector (stratagene) after being digested with the same enzyme. As a result, the pBS-st2A vector was constructed.

Example 2

Separation of Pepper PSY Gene and Bacterial CrtI Gene (2-1) Separation of Pepper PSY Gene In order to clone the phytoene synthase gene (PSY) of SEQ ID NO: 6 derived from Korean pepper, *Capsicum annuum* cv. NocKwang, total RNA was separated from roots of pepper. In detail, about 1 g of each sample was sonicated with a mixing bowl under liquid nitrogen, transferred to 2 mL tubes and extracted with 500 μL of RNA extraction buffer (50 mM sodium acetate pH 5.5, 150 mM LiCl, 5 mM EDTA, 0.5% SDS) and 500 μL of phenol. The mixture was heated at 65° C. for 10 minutes and then, stirred with a rotary shaker for 15 minutes at room temperature. Then, it was centrifuged at 10,000 rpm for 10 minutes at 4° C. to collect supernatant in a fresh tube and 500 μL of chloroform was added. This supernatant was extracted again and centrifuged to collect supernatant. Then 0.6 volume equivalence of 8 M lithium chloride (LiCl) was added and reacted at −20° C. for more than 2 hours. The resultant was centrifuged at 4° C., 12,000 rpm for 20 minutes to precipitate RNA pellet and washed once by using 4 M LiCl and 80% EtOH. The RNA pellet was dissolved in 50 μL of distilled water. The RNA eluent was quantitated by measuring optical densities at $A_{260}/A_{280}$ with a UV spectrophotometer before use. This RNA was used for template and a primer set of SEQ ID NO: 9 (Psy-Fw primer) and SEQ ID NO: 10 (Psy-Rv primer) specific for pepper PSY gene was added. Then, the pepper PSY gene was amplified by conducting reverse transcriptase-polymerase chain reaction (RT-PCR). In detail, about 2 μg of total RNA was reacted with 50 μM oligo dT primer under a condition: 55° C. 20 minutes, 99° C. 5 minutes and cooled on ice. Then, 1 μL of RNase H was treated at 37° C. for 20 minutes to synthesize cDNA with 10× RT buffer, 25 mM $MgCl_2$, 0.1 M DTT, RNase OUT, SuperScript™ RT). The synthetic cDNA was used for template and each primer was added in 10 pmol. Then, it was reacted with 10× Taq polymerase buffer (250 μM $MgCl_2$, 100 μM dNTP, 1 unit Ex-Taq polymerase (Takara) to be adjusted to 20 μL of total volume under the following condition: 94° C. 3 minutes, 94° C. 30 seconds, 60° C. 30 seconds, 72° C. 1 minute repeatedly for 30 cycles and then 75° C. 5 minutes.

As a result, the PCR product amplified above was ligated into the pCR2.1 vector (Invitrogen) for PCR cloning and the pCR2.1-Psy vector was constructed.

(2-2) Separation of Bacterial CrtI Gene

In order to clone the carotene desaturase gene (CrtI) of SEQ ID NO: 8 derived from *Erwinia uredovora* 20D3, bacterium ATCC 19321 strain was allotted from the KACC (Korean Agricultural Culture Collection). Bacterial genomic DNA was separated by using the conventional molecular cloning procedure. The genomic DNA was used for template and a primer set of SEQ ID NO: 11 (CrtI-Fw primer) and SEQ ID NO: 12 (CrtI-Rv primer) specific for bacterial CrtI gene was added in 10 pmol, respectively. Then, they were mixed with 10× Taq polymerase buffer (250 μM MgCl$_2$, 100 μM dNTP, 1 unit Ex-Taq polymerase (Takara) to be adjusted to 20 μL of total volume and reacted under the following condition: 94° C. 3 minutes, 94° C. 30 seconds, 60° C. 30 seconds, 72° C. 1 minute repeatedly for 30 cycles and then 75° C. 5 minutes.

As a result, the bacterial CrtI gene was separated. Then, the PCR product amplified above was cloned into the pGEM-T easy vector (Promega) and the pGEM-CrtI vector was constructed.

Example 3

Preparation of PAC Gene for Beta-Carotene Production (3-1) Ligation of Phytoene Synthase Gene and 2A Sequence In order to prepare the multi-cistronic PAC gene of beta-carotene-inducing PSY and CrtI genes, the recognition sites of restriction enzyme HindIII and PstI were attached first at the ends of PSY gene. In detail, the pCR2.1-Psy vector manufactured in Example 2-1 was used for template and a primer set of SEQ ID NO: 13 (5H-Psy primer) and SEQ ID NO: 14 (3P-Psy primer) was added in 10 pmol, respectively. Then, they were reacted with 10× Taq polymerase buffer (250 μM MgCl$_2$, 100 μM dNTP, 1 unit Ex-Taq polymerase (Takara) to be adjusted to 50 μL of total volume under the following condition: 94° C. 3 minutes, 94° C. 30 seconds, 60° C. 30 seconds, 72° C. 1 minute repeatedly for 30 cycles and then 75° C. 5 minutes. As a result, the PCR product was digested with restriction enzymes HindIII and PstI and then cloned into the plasmid pBS-st2A (See Example 1) at the 5'-upstream region of st2A sequence after being digested with same enzyme. The pBS-Psy-st2A vector was constructed.

(3-2) Cloning of TP Sequence

The bacterial CrtI gene needs to be connected with an additional transit peptide (Tp) moving the PSY enzyme toward a synthetic site of beta-carotene (chloroplast, starch body etc.), although plant-derived PSY genes have Tp signal naturally. Accordingly, rbcS-Tp (150 bp) gene, a rice Tp isolated from rbcS (ribulose biphophate carboxylase/oxygenase small subunit) gene, was cloned into the 5'-upstream region of CrtI gene as follows.

The pSK-RTG vector containing the rbcS gene of rice plant was used for template [Jang et al., 1999, *Mol. Breeding*, 5:453-461] and a primer set of SEQ ID NO: 15 (5P-Tp primer) and SEQ ID NO: 16 (3Nc-Tp primer) containing recognition sites of restriction enzyme PstI and NcoI at both ends of Tp sequence was added. Then, PCR reaction was conducted simply under the following condition: 94° C. 10 seconds, 60° C. 10 seconds, 72° C. 10 seconds, 72° C. 1 minute.

As a result, 160 bp of the PCR product amplified above was digested with restriction enzymes PstI and NcoI and then cloned into the pGEM-T easy vector after being digested with same enzyme. The pGEM-Tp vector was constructed.

(3-3) Ligation of TP Sequence and CrtI Gene

In order to clone the CrtI gene into the upstream region of the Tp sequence, recognition sites of restriction enzyme NcoI and ApaI were attached at both ends of CrtI gene and ligated into the pGEM-CrtI vector. The pGEM-CrtI vector was used for template and a primer set of SEQ ID NO: 17 (5Nc-CrtI primer) and SEQ ID NO: 18 (3Ap-CrtI primer) was added. Then, PCR reaction was conducted under the same condition with that of CrtI gene amplification.

1.5 kb of the PCR product was digested with restriction enzyme NcoI and ApaI and cloned into the pGEM-Tp vector at the 3'-downstream region of Tp sequence after being digested with the same enzymes. The pGEM-Tp-CrtI vector was constructed.

(3-4) Ligation of Phytoene Synthase Gene, 2A Sequence and Carotene Desaturase Gene The Tp-CrtI gene fragment contained in the pGEM-Tp-CrtI vector was inserted at the 3'-downstream region of Psy-st2A gene contained in the pBS-Psy-st2A vector in frame with its coding frame. First, recognition sites of restriction enzyme SmaI and XbaI were attached at both ends of Tp-CrtI gene. The Tp-CrtI gene was cloned into the pBS-Psy-st2A vector. In detail, the pGEM-Tp-CrtI vector was used for template and a primer set of SEQ ID NO: 19 (5Sm-TpCrtI primer) and SEQ ID NO: 20 (3Xb-TpCrtI primer) was added. Then, PCR reaction was conducted under the same condition with that of CrtI gene amplification.

1.642 kb of the PCR product was digested with restriction enzyme SmaI and XbaI and cloned into the pBS-Psy-st2A vector at the 3'-downstream region of Psy-st2A sequence after being digested with the same enzymes. The pBS-Psy-st2 A-Tp-CrtI, that is to say the pBS-PAC vector was constructed. As a result, the final PAC fusion gene is identified to have 2,952 bp of total nucleotide sequence (SEQ ID NO: 1) by performing a sequencing analysis of total nucleotide sequences once more.

Example 4

Construction of Recombinant Vector for Rice Transformation and Transformation of *Agrobacterium*

(4-1) Construction of Recombinant Vector for Rice Transformation

In order to construct a recombinant vector for rice transformation inducing rice endosperm-specific expression, the pBS-PAC vector prepared in Example 3 was used for template and a primer set of SEQ ID NO: 21 (PAC-B1 primer) and SEQ ID NO: 13 (PAC-B2 primer) was added in 10 pmol, respectively. Then, they were mixed with 10× Taq polymerase buffer (250 μM MgCl$_2$, 100 μM dNTP, 1 unit Pyrobest polymerase (Takara) to be adjusted to 50 μL of total volume and reacted for PCR amplification under the following condition: 94° C. 3 minutes, 95° C. 30 seconds, 60° C. 30 seconds, 68° C. 1 minute repeatedly for 30 cycles and then 68° C. 10 minutes. In this case, the primer set of SEQ ID NO: 21 and SEQ ID NO: 13 was designed in order to contain a part of bacterial specific nucleotide sequences (attB1 and attB2) at both ends (12 bp respectively). Therefore, PAC gene can be amplified specifically when bacteriophage infects bacteria.

The PCR product (2,976 bp) amplified above was used for template and a primer set of SEQ ID NO: 25 (attB1 primer) and SEQ ID NO: 26 (attB2 primer) was added in 2 pmol, respectively. Then, they were mixed with 10× Taq polymerase buffer (250 μM MgCl$_2$, 100 μM dNTP, 1 unit Pyrobest polymerase (Takara) to be adjusted to 50 μL of total volume and reacted for PCR amplification under the following condition: 95° C. 3 minutes, 94° C. 30 seconds, 45° C. 30 seconds, 68° C. 2 minute repeatedly for 5 cycles; then, 94° C. 30 seconds, 55° C. 30 seconds, 68° C. 2 minute repeatedly for 20 cycles; and then 68° C. 10 minutes. In this case, the primer set of SEQ ID NO: 23 and SEQ ID NO: was designed in order to contain whole bacterial specific nucleotide sequences (attB1 and attB2) at both ends (29 bp respectively) after recombinant bacteriopharge infects bacteria.

The PCR product containing bacterial specific nucleotide sequences (attB1 and attB2) at both ends after recombinant bacteriophage infects bacteria, was primarily reacted at 25° C. for an hour with the pDONR201 vector (Invitrogen) containing bacteriophage-specific nucleotide sequences (attP1 and attP2) at both ends after recombinant bacteriophage infects bacteria, while adding BP clonase enzyme (Invitrogen). Through this BP reaction, the pENTR-PAC vector was constructed.

In order to clone PAC gene contained in the pENTR-PAC vector into a final vehicle for rice plant transformation, the pMJ-103 vector (Green Gene Bio) manufactured at Myungji University was secondarily reacted at 25° C. for an hour while adding LR clonase enzyme (Invitrogen). Through this so-called LR reaction, the pGlb-PAC vector (See FIG. 1) for rice plant transformation was constructed. In this case, the pMJ-103 vector is a sort of gateway vehicle that contains rice endosperm-specific globulin (Glb) promoter, potato protease inhibitor II (PinII) terminator and herbicide resistance Bar gene from the downstream of 35S promoter as a plant selective marker, while its backbone is the pSB11 vector, a super-binary plasmid having spectinomycin resistance gene as a selective marker.

(4-2) Transformation of *Agrobacterium*

In order to introduce the pGlb-PAC vector into *Agrobacterium* for rice transformation, a conventional method (tri-parental mating) was used. In detail, *Agrobacterium tumefaciens* LBA4404 transformed with the pSB1 vector containing a super-binary plasmid including a vir gene was cultured onto an AB culture plate adding tetracycline (10 mg/L) for 2 to 3 days at 28° C. *E. coli* HB101 containing the pRK201, a conjugal helper plasmid and *E. coli* DH-5α containing the pGlb-PAC vector were cultivated onto LB plates adding kanamycin (50 mg/L) and spectinomycin (50 mg/L) respectively at 37° C. overnight so as to collect total 3 kinds of colonies.

The 3 kinds of colonies were mixed and cultured onto a nutrient agar plate (Difco) at 28° C. overnight. The resulting bacteria were diluted 10-fold with culture broth (or water), streaked for single cell isolation onto an AB culture plate (AB-st) adding spectinomycin (50 mg/L) and tetracycline (10 mg/L) and cultured for 3 days at 28° C. Single colonies appearing onto the AB culture plate (AB-st) were streaked once more and cultured for 3 days at 28° C. to select a final single colony (*Agrobacterium tumefaciens* LBA4404 pGlb-PAC). The resulting *Agrobacterium* was inoculated into YEP culture broth (YEP-st) adding spectinomycin (50 mg/L) and tetracycline (10 mg/L) and cultured with shaking at 28° C. for 2 days. Then, plasmids were isolated in order to analyze a pattern of restriction digestion. As a result, it is re-identified that *Agrobacterium* be transformed with pGlb-PAC gene. Next, the *Agrobacterium tumefaciens* LBA4404 pGlb-PAC was used to transform a rice plant.

Example 5

Transformation of Rice Plant Using *Agrobacterium*

In order to transform a rice plant, mature seeds were used. Above all, seeds of a rice plant (Nakdong) were peeled off, soaked in 70% ethanol for 1 minute, washed 2 to 3 times with distilled water and sterilized on the surface with 2% sodium hypochloride (commercial "ROX" product) solution while stirred for 20 minutes. Then, the resulting seeds were sterilized 4 to 5 times with distilled water, dried with filter paper and placed onto a callus-inducing plate (N6 basic media, 500 mg/L proline, 500 mg/L glutamine, 3% sucrose, 2 mg/L 2,4-D, 0.25% phytagel, pH 5.8). The resulting seed was cultivated at 28° C. under a dark condition for 4 to 5 weeks to generate a callus. Then, only embryogenic callus was selected to re-differentiate into a transformed plant.

The *Agrobacterium tumefaciens* LBA4404 pGlb-PAC transformed with the pGlb-PAC vector was cultured for 30 hours and diluted with AAM culture broth (containing 100 mM acetosyringone) until reaching OD600 1.0 to 1.2 of cell concentration. Then, the *Agrobacterium* was incubated with the embryogenic callus for 15 minutes. The resulting callus was dried onto a sterilized filter paper and co-cultured on a co-culture plate (N6 basic media, 500 mg/L proline, 500 mg/L glutamine, 3% sucrose, 2 mg/L 2,4-D, 100 mM acetosyringone, 0.25% phytagel) at 24° C. under a dark condition for 2 to 3 days.

In order to remove *Agrobacterium* remaining on the surface, the co-cultured callus was washed with AAM culture broth containing cefotaxime (250 mg/L), covered with a sterilized filter paper while removing moisture, and transferred on a selective medium (N6 basic medium, 500 mg/L proline, 500 mg/L glutamine, 3% sucrose, 2 mg/L 2,4-D, 0.25% phytagel, 6 mg/L phosphinothricin, 250 mg/L cefotaxime, pH 5.8) to collect only transformed calluses. Then, the resulting callus was sub-cultured with fresh selective media every 2 weeks, and after 5 weeks, re-cultured with culture medium for plant re-differentiation (MS basic medium, 3% sucrose, 0.5 mg/L NAA (naphthaleneacetic acid), 2 mg/L kinetin, 250 mg/L cefotaxime, 3 mg/L phosphinothricin, 0.3% phytagel, pH 5.8). After being induced, the resulting plant was refined in MS medium under an aerated condition.

The conditions of culture media used in each step are illustrated in following Table 1.

TABLE 1

| | Sp. | | | | | |
|---|---|---|---|---|---|---|
| | Callus induc. | Pre-culture | Co-culture of *Agrobacterium* | Callus selection | Plant induction | Refinement |
| Seed | N6 basic media 2,4-D 2 mg/L | N6 basic media 2,4-D 2 mg/L | N6 basic media 2,4-D 2 mg/L | N6 basic media 2,4-D 2 mg/L PPT 6 mg/L | MS basic media NAA 0.5 mg/L kinetin 2 mg/L PPT 3 mg/L | MS basic media |
| Time | 4-5 days | 2-3 days | 2-3 days | 5 weeks | 2-4 weeks | 1-2 weeks |
| Anti-biotic condition | | None | | Cefotaxime 250 mg/L | Cefotaxime 250 mg/L | Cefotaxime 250 mg/L |

The plants grown above were collected out of culture bottles. The roots were washed with water, transferred into a fresh plastic bottle filled with soil of rice field and incubated in a green house.

Example 6

Identification of Seeds Harvested from Transformed Rice Plant 10 of the re-differentiated rice plants transformed with the pGlb-PAC gene obtained above (PAC2-1, 2-2, 4-2, 4-3, 5, 7, 8, 9, 10 and 11) were compared according to yellow color of seeds, because they are re-differentiated at different stages—PAC2-1, 2-2, 4-2 and 4-3 lines produced beta-carotene at T3 seeds, PAC9, 10 and 11 lines at T2 seeds and PAC5, 7 and 8 lines at T1 seeds.

After harvesting mature seeds of each line, they were peeled off with a rice husker (TR-200 Electromotion rice husker, Kett product) and then, polished with a rice polisher for 1 minute to remove aleurone layer (Pearlest polisher, Kett). These polished rice was compared one another.

Figure 3:
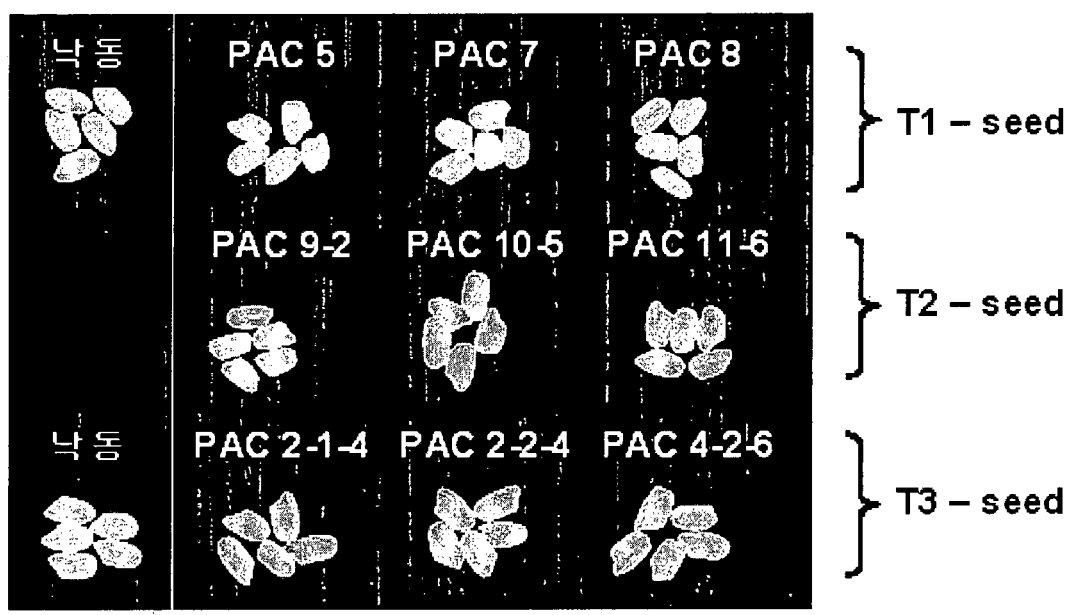
FIG. 3 is T1, T2 and T3-generation mature seeds collected from the rice endosperm that is transformed with the multicistronic pGlb-PAC vector to produce beta-carotene and appears yellow color.

As a result, it is observed that PAC10, 11, 2-1, 2-2 and 4-2 (4-3) lines appear yellow color similarly regardless of T2 or T3 generation as described in FIG. 3. In the T2-generation, PAC9 appeared weaker yellow than PAC10 and 11. Further, PAC5, 7 and 8 of T1 generation tended to show weak yellow.

Example 7

Analysis of Plant Transformation (7-1) Analysis of Transformation by PCR

Among transformed rice plants, PAC9, 10, 11, 2-1, 2-2, 4-2 and 4-3 were collected with leaf tissues. Then, genomic DNAs was separated and purified by using Genomic DNA Purification Kit (I.J. BIO DNA System). The resulting DNA eluant was quantitated by measuring optical densities at A260/A280 with a UV spectrometer. 100 ng of the genomic DNA was used for template and a primer set of SEQ ID NO: 25 (Psy-CT-Fw primer) and SEQ ID NO: 26 (CrtI-NT-Rv primer) was added to conduct a PCR reaction (94° C. 2 minutes; 95° C. 30 seconds, 55° C. 30 seconds and 72° C. 30 seconds repeatedly for 30 cycles and 72° C. 5 minutes).

As a result, 370 bp of the PCR product was observed in the transformed rice plants of the present invention. Therefore, it is identified that each line be completely transformed.

(7-2) Analysis of Transformation by Southern Blot

The genomic DNA isolated in Example (7-1) was digested in 5 μg with restriction enzyme XbaI and analyzed by conducting an agarose gel electrophoresis through a conventional procedure of Southern blot. Then, it was transferred onto an NC (nitrocellulose) membrane by a capillary reaction and blotted by using 1.5 kb of $^{32}$P-labelled CrtI gene for probe.

Figure 4:
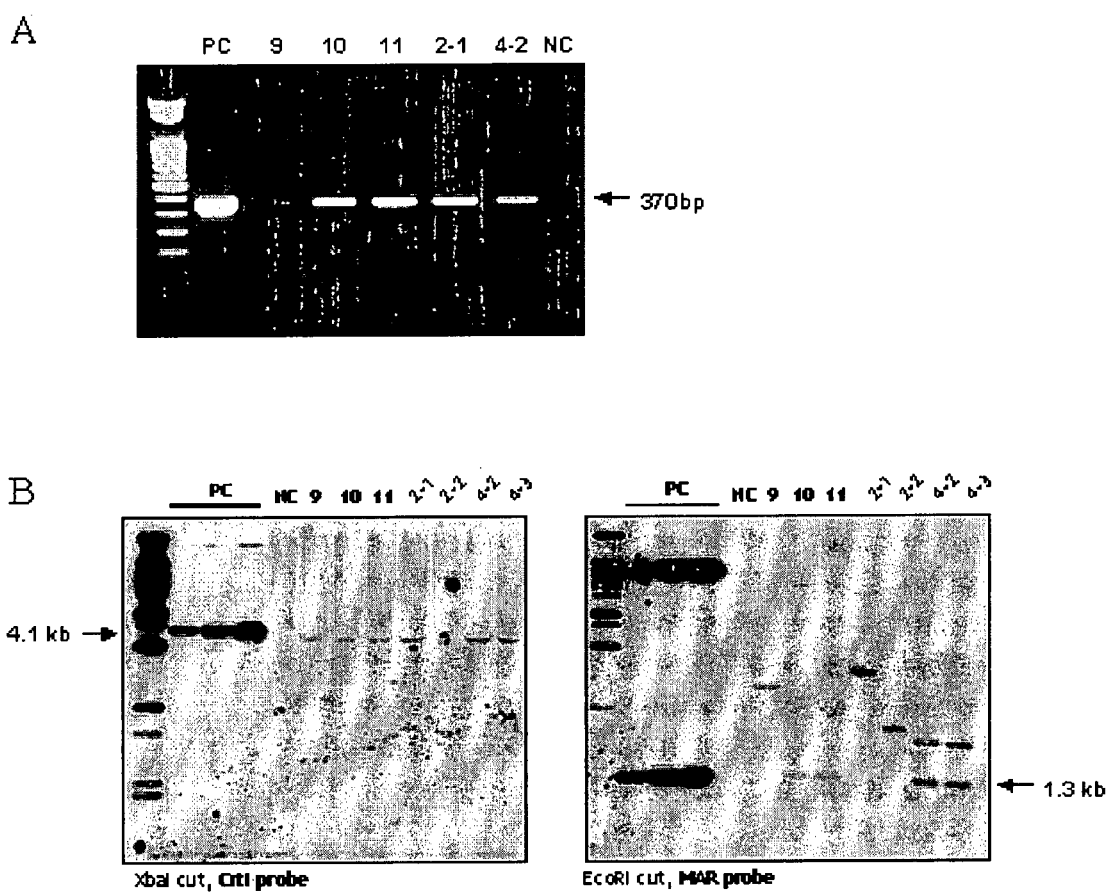
FIG. 4 is a cell transformation of the plant identified by performing PCR (A) and Southern blot (B) (M, 1 kb ladder DNA size marker; PC, pGlb-PAC plasmid DNA; NC, non-transgenic control rice plant (Nakdong); 9, 10, 11, 2-1, 2-2, 4-2, 4-3, pGlb-PAC rice plant transformants)

As a result, 4.1 kb of insert gene was observed in PAC 9, 10, 11, 2-1, 4-2 and 4-3 excepting PAC 2-2 as described in FIG. 4B (left).

Furthermore, in order to calculate a gene copy number by performing a Southern blot, the same genomic DNA was digested in 5 μg with restriction enzyme EcoRI, analyzed by conducting an agarose gel electrophoresis, transferred onto an NC membrane and blotted by using 1.5 kb of $^{32}$P-labelled CrtI gene for probe.

Therefore, as described in FIG. 4B (right), PAC4-2 and PAC4-3 were proved as the same lines because they had the same signal pattern. Also, PAC10 and 11 showed two Mar signal bands (left border: 1.3 kb of Mar signal band; right border: Mar signal bands different in the size according to insertion sites because rice genomic DNA was digested at an unknown site with restriction enzyme EcoRI) clearly. By using Mar gene for probe, this result proved an insertion of one copy gene. Besides, PAC9, 2-1 and 2-2 showed 1, 2 and 1 Mar signal bands respectively and estimated to have one copy insertion. Otherwise, it is guessed that they may provoke a rearrangement of inserted genes while transforming genomic DNA of rice plant.

Example 8

Analysis of Gene Expression of Plant Transformant

Total RNA was separated from rice harvested in the transformed plant and analyzed to examine an expression of PAC gene according to multi-cistronic sites by conducting RT-PCR. In detail, in order to separate total RNA, 1 g rice sample of each line was soaked for about 2 hours, powdered with a mixing bowl under a liquid nitrogen sufficiently and mixed with 5 mL of RNA extraction buffer [200 mM Tris-HCl (pH 9.0), 400 mM LiCl, 25 mM EDTA (pH 8.2), 1% SDS] and 5 mL of phenol. The mixture was transferred to a 15 mL tube, centrifuged at 3,000 rpm for 10 minutes and supernatant layer was carefully transferred to a fresh tube. Then, 1 mL of chloroform and 1 mL of phenol were added, mixed with vortexing and centrifuged again at 3,000 rpm for 10 minutes to collect supernatant. After that, the supernatant was carefully transferred to a fresh tube and mixed sufficiently with vortexing after adding 2 mL of chloroform to extract the solution. This procedure was repeated twice. The resulting supernatant was transferred to a fresh tube and stored at −20° C. for an hour after adding 2.5 volume equivalence of ethanol and 0.1 volume equivalence of 3 M (sodium acetate, pH 5.2). Then, it was centrifuged at 4° C., 12,000 rpm for 10 minutes to collect DNA and RNA pellets, dissolved in 2 M lithium chloride (LiCl) solution and incubated at −20° C. for more than 2 hours to precipitate RNA. The RNA pellet was washed once with 80% EtOH and dissolved in 80 to 100 μL of DEPC solution. The RNA extract was quantitated by measuring optical densities at A260/A280 with a UV spectrophotometer in order to perform an mRNA selective RT-PCR.

1 μg of the total RNA was used for template and amplified with a commercial kit (TAKARA mRNA selective RT-PCR kit [1× RT buffer, 5 mM MgCl$_2$, 1 mM dNTP, 50 μM Oligo dT primer, RNase inhibitor (0.8 unit/μL), AMV RTase XL (0.1 unit/μL)] (Takara, Japan). In order to synthesize cDNA, it was reacted at 30° C. for 10 minutes and at 42° C. for 30 minutes and cooled at 4° C. The synthetic cDNA was reacted with following primer sets. Precisely, PST gene-specific primer set of SEQ ID NO: 9 and SEQ ID NO: 10; Tp-CrtI gene-specific primer set of SEQ ID NO: 19 and SEQ ID NO: 20; a primer set specific for SL (small-length) of st2A sequence of PAC gene with SEQ ID NO: 25 and SEQ ID NO: 26; a primer set of SEQ ID NO: 27 and SEQ ID NO: 28 amplifying total length of PAC gene (PAIC-F1 and PAIC-R1 primers); and a rice glutelin specific primer set of SEQ ID NO: 29 and SEQ ID NO: 30 confirming a fixed relative amount of RNA were added in 10 pmol, respectively. Then, they were mixed with 10× Taq polymerase buffer (250 μM MgCl$_2$, 100 μM dNTP, 1 unit Pyrobest polymerase (Takara)) to be adjusted to 50 μL of total volume and reacted for PCR amplification under the following condition: 94° C. 3 minutes, 95° C. 30 seconds, 55° C. 30 seconds, 72° C. 1 minute repeatedly for 30 cycles and then 68° C. 10 minutes. Especially, the amplification step at 72° C. was controlled according to lengths of synthetic genes and adjusted to 1 minutes in Psy gene, 1.5 minutes in Tp-CrtI gene, 30 seconds in PAC_SL gene, 3 minutes in PAC_FL and 30 seconds in glutelin.

Figure 5:
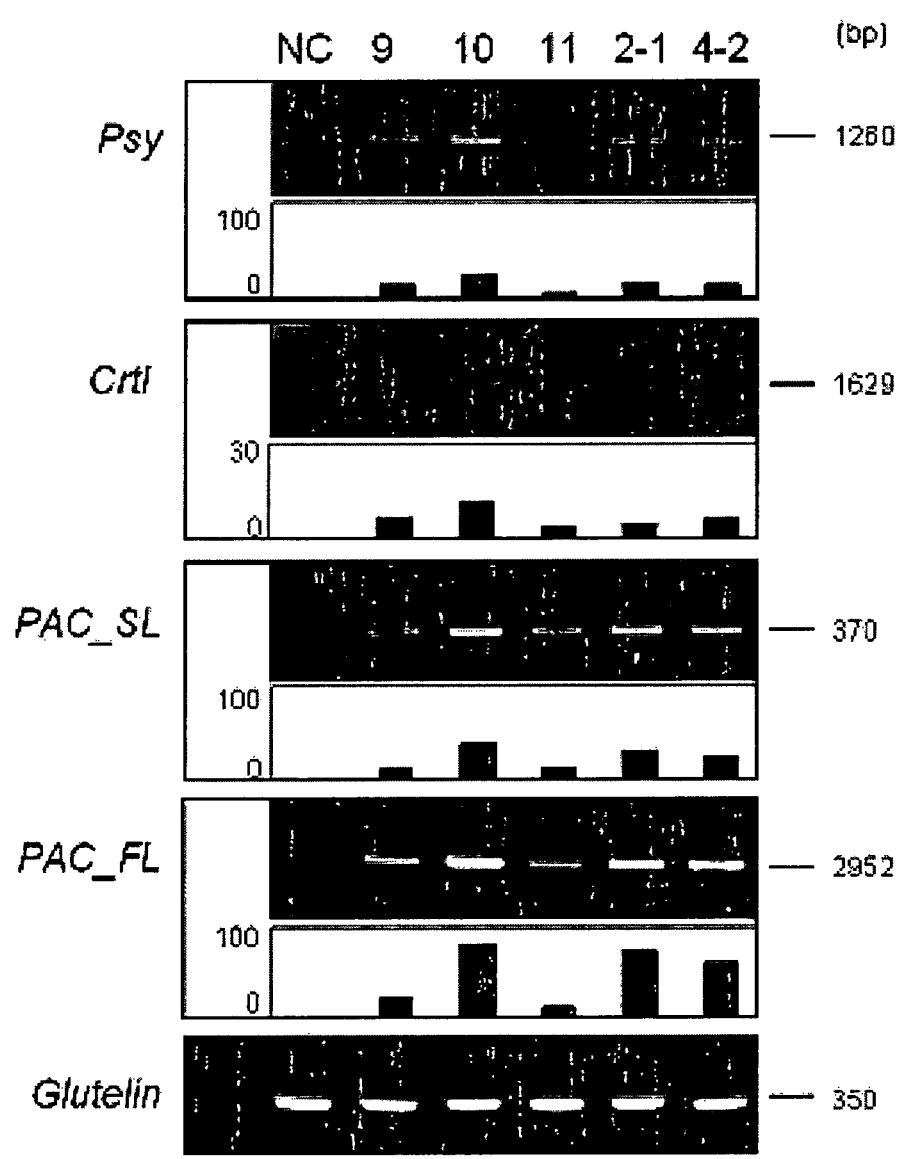
FIG. 5 is a gene expression in the plant of the present invention identified by performing an RT-PCR.

As a result, all transcripts of Psy gene, CrtI gene, PAC_SL gene, PAC_FL gene were not detected in intact rice seeds (Nakdong), but the all transcripts were clearly detected in transformed rice seeds respectively at estimated sizes as described in FIG. 5. When using glutelin as a control group, the degrees of gene expression were compared in 4 sites of the PAC transformant. It is observed to decrease in an order of 10>2-1>4-2>9>11 lines in spite of some differences.

Example 9

Separation of Plant Seed and Western Blot Analysis

Crude protein was separated from rice harvested in transformed rice plant and analyzed to measure a degree of translation and accumulation of exogenous PAC protein. In detail, in order to separate seed proteins, 2 grains of each rice line were soaked with water for about 2 hours, powdered and mixed with 200 µL of urea sample buffer [0.025 M Tris (pH 8.8), 4.0% (W/V) SDS, 4.0 M Urea, 5% (v/v) 2-mercaptoethanol]. The resulting solution was vortexed sufficiently for 30 minutes, centrifuged at 4° C., 13,000 rpm for 60 minutes and carefully transferred to a fresh tube.

The protein extracted above was quantitated, centrifuged in 20 µg by using 7.5% Gradi-Gel™ II (ElpisBio) PAGE and transferred onto a nitrocellulose membrane by a semidry method in order to perform a Western blot. Then, the resulting membrane was coated with 5% skim milk and reacted in TBS buffer [20 mM Tris-HCl (pH 7.5), 137 mM NaCl] containing 1% Tween-20 for 4 hours, while adding anti-PSY polyclonal antibody (obtained from Dr. Bile Camara, France) at 1,000:1 of dilution. After the reaction, it was washed with TBS buffer for 10 minutes and this was repeated four times. The resulting membrane was reacted with alkaline phosphatase (AP)-conjugated secondary antibody at 6,000:1 of dilution for an hour, washed with TBS buffer four times and transferred into a plastic bag to appear color. Chromogenic substrate mixture (33 µL of NBT, 16.5 µL of BCIP in 5 mL of alkaline phosphatase buffer; Promega) was coated uniformly onto the membrane and a degree of coloring was observed. At a proper coloring, stopping solution [200 µL of 0.5 M EDTA (pH 8.0) in 50 mL of TBS] was added and dried at room temperature.

Figure 6:
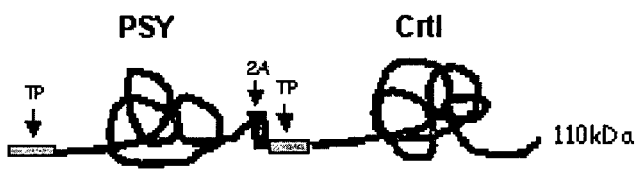
FIG. 6 is a protein expression in the plant of the present invention identified by performing a Western blot (GF: green fruit of pepper; RF: red fruit of pepper)
Figure 6:
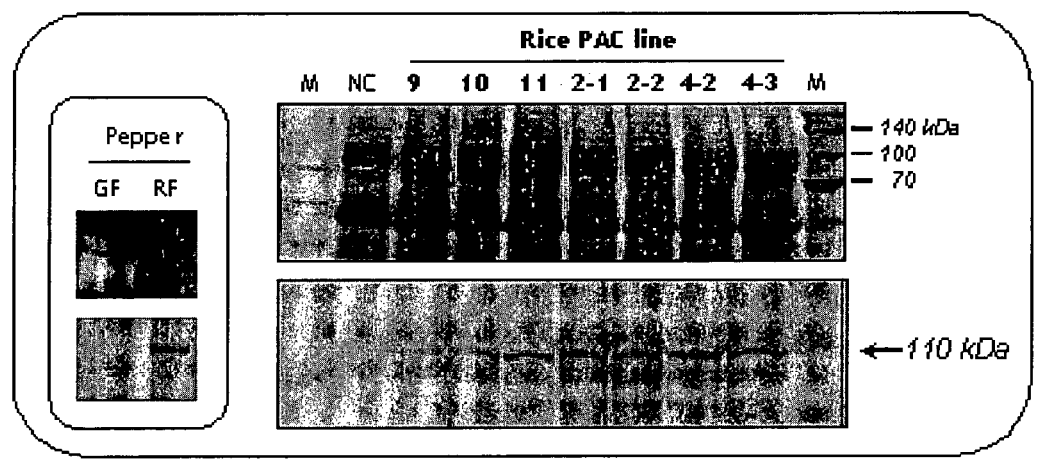
Figure 7:
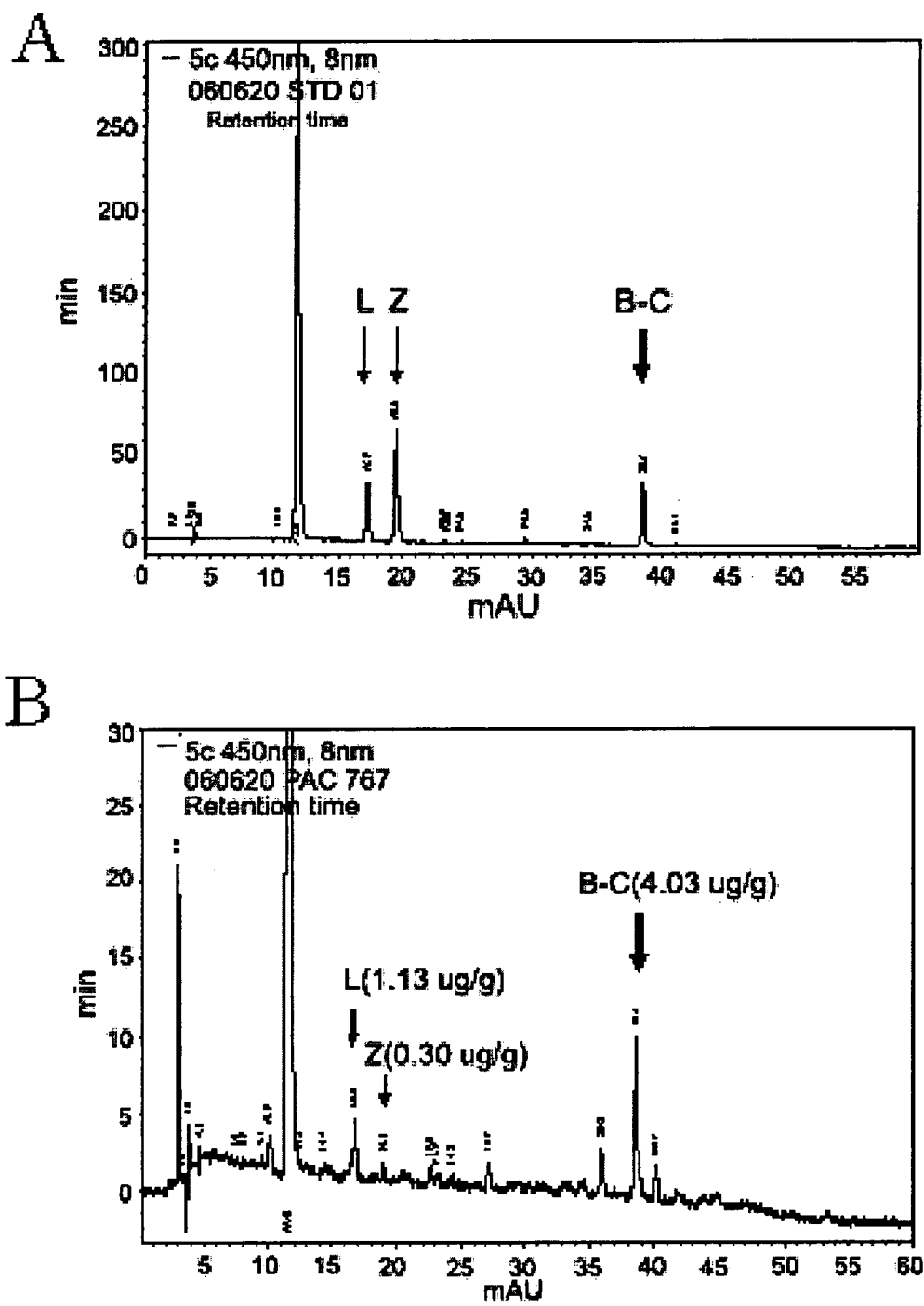
FIG. 7 is a production of beta-carotene in the plant of the present invention identified by an HPLC analysis (L, lutein; Z, zeaxanthin; B-C, beta-carotene)
Figure 8:
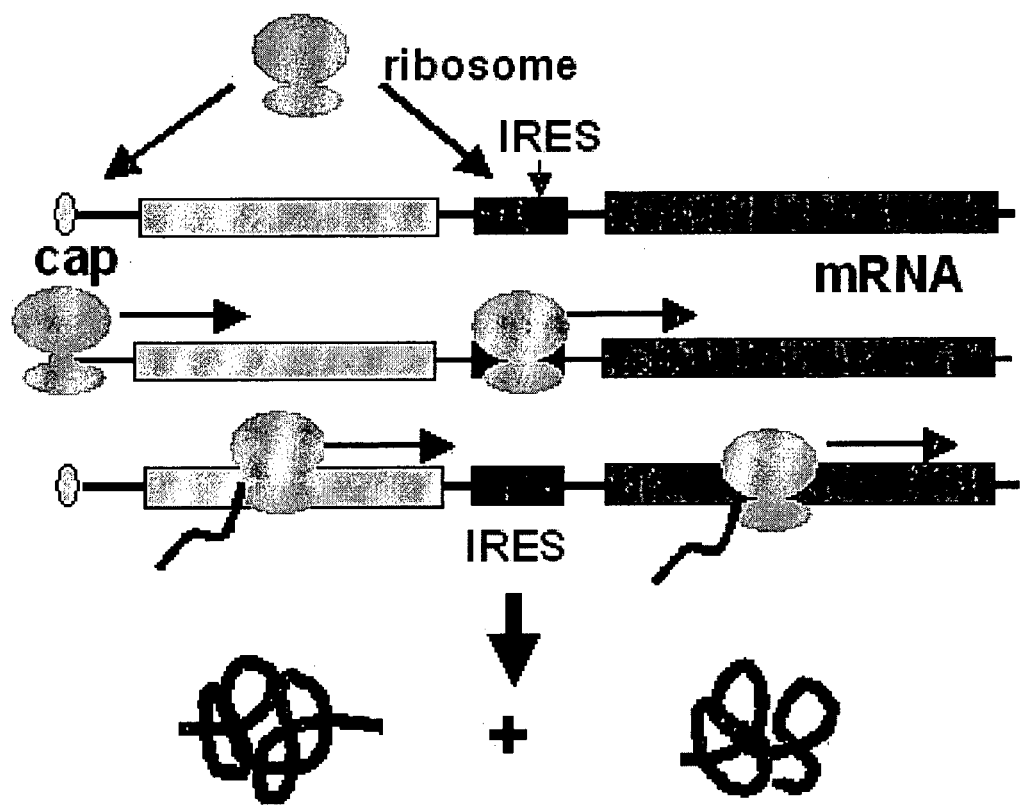
FIG. 8 is a schematic co-expression of two independent genes from the promoter of internal ribosome entry site.

As a result, as described in FIG. 6, the expression of PSY protein was detected around 110 kDa of estimated region and accumulated in a relatively similar amount although it was slightly high in PAC2-1 line.

Example 10

Measurement of Carotenoid Content in Plant Seed (10-1) Measurement of Carotenoid Content in Plant Seed I Extraction of carotenoid, quantitation by HPLC and the like were accomplished by modifying the procedure of Minguez-Mosquera et al. [Minguez-Mosquera et al., *J. Agric. Food Chem.*, 41, 1616, 1993].

In order to extract carotenoid and carotenoid ester, 3 g of rice harvested from general rice (Nakdong) and transformed rice PAC4-2 were powdered respectively using a mixer. 200 mL of chloroform, 250 mL of tertiary distilled water, 1 mL of 1% BHT (butylated hydroxytoluene in MeOH) solution and 1 mL of standard substance (Sudan II) were added with stirring and filtrated. This procedure was repeated 2 to 3 times to collect extracted solution. Then, sodium sulfate anhydrous was added to the extracted solution in order to remove moisture. The resulting solution was concentrated with a rotary evaporator, resuspended with 50 mL of ethyl ether and then, saponified at room temperature for 16 hours by adding 2.5 mL of saturated KOH solution. In order to remove alkali, solvent was fractionated with 50 mL of distilled water and treated on an ethyl ether layer with sodium sulfate anhydrous to remove moisture. After that, the resultant was concentrated, dissolved in 1 mL of MeOH:TBME (tert-butyl methyl ether) (1:1, v/v) solution containing 1% BHT and filtrated with a 0.45 µm filter. The sample was stored in a vial before HPLC analysis.

The HPLC was conducted on PDA (SPD-M10Avp) and YMC (3 µm-$C_m$-reversed phase, 250×4.6 mm) column and precolumn (Delta-pak $C_{18}$ 5 µm 100 Å, Waters), equipped with Shimadzu 10Avp pump and controller. Solvent A (MeOH-MTBE-water-triethyl amine, 90:6:4:0.1, v/v/v) and solvent B (MeOH-MTBE-water-triethyl amine, 6:90:4:0.1, v/v/v) were used as mobile phase. Isocratic solvent A was run down under a gradient condition until reaching 100% after 15 minutes, changed to 100% solvent B after 40 minutes, changed again to solution A after 45 minutes and stabilized after 50 minutes. At 450 nm of wavelength and 0.8 mL/min of flow rate, 30 µL of sample was loaded and the analytic data was measured by using the following formula.

Content(unit:µg/100 g)=(sample area×internal std of use amount (0.5 mg)×conversion factor (100000))/(internal std area×sample amount used(3 g))

In this case, most of standard substances excluding sudan II, α- and β-carotene (Sigma) were obtained from Extrasynthese. They were manipulated under a dark condition and 1% BHT was added to all the solvent to prevent acidification. The solution was wrapped with aluminum foil and stored at −20° C. before use.

As a result, the PAC4-2 line was observed to contain considerable amount of total carotenoids (548 µg/100 g) and especially beta-carotene (403 µg/100 g) in 74%, when standard carotenoids (lutein, zeaxantin, beta-carotene and the like) were examined.

(10-2) Measurement of Carotenoid Content in Plant Seed II

In order to obtain more objective data of contents, samples of transformed rice (general Nakdong, PAC2-1 and PAC4-2) were primarily requested to Korea Food Research Institute, an authorized organization for food analysis to perform analysis of beta-carotene. Then, 4 samples of transformed rice (general Nakdong, PAC4-2, PAC10-3 and PAC11-2) were secondarily requested to the Korea Food Research Institute for food analysis to perform analysis of beta-carotene [Food Code (2006), Analysis of Trace Nutrients].

As a result, PAC2-1 and PAC2-1 lines were observed to include 0.474 mg/100 g and 0.536 mg/100 g of beta-carotene level, respectively, in a primary analysis, but beta-carotene was not detected at all in general rice plant (Nakdong). In a secondary analysis, PAC4-2, PAC10-3 and PAC11-2 were examined to include 1.271 mg/100 g, 1.000 mg/100 g and 0.910 mg/100 g of beta-carotene level, respectively. Therefore, it is identified that beta-carotene was produced in about 0.5 to 1.3 mg per 100 g of rice when introducing the multicistronic recombinant PAC gene of the present invention.

Example 11

Synthesis of Internal Ribosome Entry Site Derived from CrTMV (Crucifer-Infecting Tobamovirus)

Internal ribosome entry site is a mechanism replacing a cap structure, a general eukaryotic translation mechanism and found in virus, insect, animal and the like. CrTMV-IRES sequence (SEQ ID NO: 31) is derived from CrTMV (crucifer-infecting tobamovirus), a plant virus and corresponds to 150 bp-upstream of coat protein. In order to synthesize the CrTMV-IRES sequence, 4 kinds of primers that are composed of 53, 53, 54 and 56 mer overlapped in 21, 20 and 25 mer respectively were designed (1F, SEQ ID NO: 32; 2R, SEQ ID NO: 33; 3F, SEQ ID NO: 32; 4R, SEQ ID NO: 32).

1F
(5'-ACGAATTCGTCGATTCGGTTGCAGCATTTAAAGCGGTTGACAACTTTAAAAGA-3': SEQ ID NO: 32), 2R
(5'-ACTACACCCTTTTCTTCAACCTTCTTTTTCCTTCTTTTAAAGTTGTCAACCGC-3': SEQ ID NO: 33), 3F
(5'-GTTGAAGAAAAGGGTGTAGTAAGTAAGTATAAGTACAGACCGGAGAAGTACGCC-3': SEQ ID NO: 34),
and 4R
(5'-TTTCTTCTTTCAAATTAAACGAATCAGGACCGGCGTACTTCTCCGGTCTGTACTTA-3': SEQ ID NO: 35)

Each synthetic primer was diluted to 40 pmole/μL. Then, reaction mixture containing 1 μL of each 1F and 4R primer and 2 μL of each 2R and 3F primer for substrate and primer were prepared and reacted for PCR amplification under the following condition: 95° C. 10 seconds, 58° C. 10 seconds, 72° C. 10 seconds repeatedly for 35 cycles. The resulting 150 bp of PCR product was ligated into the pGEM-T easy vector (Promega) and analyzed by performing a nucleotide sequencing. The pCrTMV-IRES vector was constructed and used in following experiments.

Example 12

Cloning of Multi-Cistronic PIC Gene for Production of Beta-Carotene

In order to prepare multi-cistronic PIC gene of PSY and CrtI producing beta-carotenes, transit peptide (Tp) that is a transfer signal necessary to move CrtI enzyme protein toward a biosynthetic site (plastids such as chloroplast and starch body) of beta-carotene needs to be linked in addition to bacterial CrtI gene. Therefore, 150 bp of Tp gene derived from rice ribulose biphosphate carboxylase/oxygenase small subunit (rbcS-Tp) was connected at the 5'-upstream region of CrtI gene. For this purpose, the pSK-RTG vector containing the rice rbcS gene was used for template and a primer set of SEQ ID NO: 36 (5PTp primer) and SEQ ID NO: 37 (3Nc-Tp primer) containing recognition sites of restriction enzyme PstI and NcoI at both ends was added to perform a PCR. Then, 160 bp of the PCR product was digested with restriction enzyme PstI and NcoI and ligated into the pGEM-T easy vector. As a result, the pGEM-Tp vector was constructed.

In order to connect CrtI gene at the downstream of Tp sequence, recognition sites of restriction enzyme NcoI and ApaI were added at both ends of CrtI gene. In detail, the pGEM-CrtI vector was used for template and a primer set of SEQ ID NO: 38 (5Nc-CrtI primer) and SEQ ID NO: 39 (3Ap-CrtI primer) was added to perform a PCR. Then, 1.5 kb of the PCR product was digested with restriction enzyme NcoI and ApaI and ligated into the pGEM-Tp vector at the 3'-downstream of Tp sequence after being digested with the same enzymes. As a result, the pGEM-Tp-CrtI vector was constructed.

In order to attach recognition sites of restriction enzyme SacI and BamHI at the terminus of CrTMV-IRES gene, the pCrTMV-IRES vector was used for template and a primer set of SEQ ID NO: 40 (5SacIRES primer) and SEQ ID NO: 41 (3SacBamIRES primer) was added to perform a PCR. Then, the PCR product was digested with restriction enzyme SacI and ligated into the pGEM-Tp-CrtI vector after being digested with the same enzymes. As a result, the pGEM-IRES-TpCrtI vector was constructed.

In order to clone Psy gene at the upstream of CrTMV-IRES gene, the pCR2.1-Psy vector was digested with restriction enzyme EcoRI to separate 1,257 bp of Psy gene and ligated into the pGEM-IRES-TpCrtI vector after being digested with the same enzymes. Then, the nucleotide sequence was analyzed. As a result, the pGEM-Psy-IRES-TpCrtI (or the pGEM-PIC vector) was constructed. The nucleotide sequence of whole PIC gene was composed of 3,077 bp (SEQ ID NO: 42).

Example 13

Construction of Plasmid for Rice Transformation

In order to construct a plasmid vector inducing rice endosperm-specific expression for rice transformation, the pGEM-PIC vector was used for template and a primer set of SEQ ID NO: 43 (PIC-B1 primer) and SEQ ID NO: 44 (PIC-B2 primer) was designed in order to contain a part of bacterial specific nucleotide sequences (attB1 and attB2) at both ends (12 bp respectively). Therefore, PIC gene can be amplified specifically when bacteriophage infects bacteria. PCR reaction was performed to amplify 3,101 bp of PIC gene.

The PCR product of PIC gene amplified above with the primer set (PIC-B1 and PIC-B2 primers) was reacted again by using a primer set of SEQ ID NO: 45 (attB1 primer) and SEQ ID NO: 46 (attB2 primer) that are designed to contain whole nucleotides of bacterial specific sequence (29 bp respectively) when bacteriophage infects bacteria.

The resulting PCR product was cloned into the pDONR221 vector (Invitrogen) containing bacteriophage specific sequence (attP1 and attP2) when bacteriopharge infects bacteria. Through this BP reaction, the pENTR-PIC vector was constructed.

Figure 9:
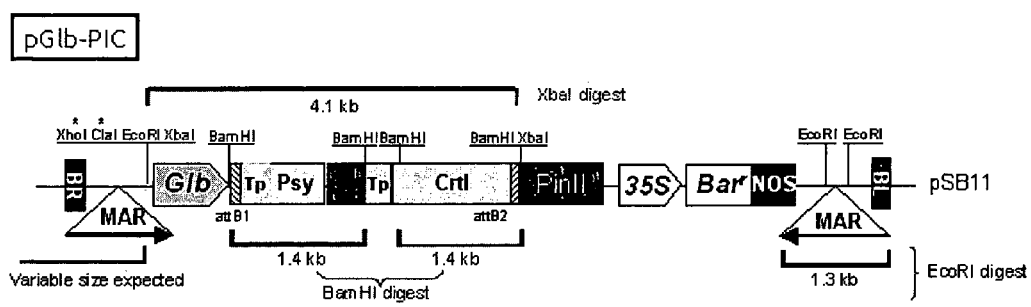
FIG. 9 is a detailed construct (genetic scheme) of the rice endosperm-specific pGlb-PIC vector containing the multicistronic PIC gene for beta-carotene production (LB: left board; RB: right board; Glb: rice endosperm-specific globulin promoter; Psy: phytoene synthase gene derived from Korean pepper NocKgwang; IRES: internal ribosome entry site; Tp: chloroplast target transit peptide gene; CrtI: bacterial carotene desaturase gene; PinII: potato protease inhibitor II terminator; P35S: CaMV 35S promoter; Bar: phosphino thricin acetyl transferase gene; NOS: nopaline synthase terminator; and MAR: matrix attachment region)

In order to transfer the PIC gene contained in the pENTR-PIC vector into a final vehicle for rice plant transformation, the pMJ-103 vector was reacted through an LR reaction to construct the pGlb-PIC vector (See FIG. 9) for plant transformation. In this case, the pMJ-103 vector is a sort of gateway vehicle that contains rice endosperm-specific globulin (Glb) promoter, potato protease inhibitor II (PinII) terminator and herbicide resistance Bar gene from the downstream of 35S promoter as a plant selective marker, while its backbone is the pSB11 vector, a super-binary plasmid having spectinomycin resistance gene as a selective marker.

In order to introduce the pGlb-PIC vector into *Agrobacterium* for rice transformation, a conventional method (tri-parental mating) was used. In detail, *Agrobacterium tumefa*-

*ciens* LBA4404 transformed with the pSB1 vector containing a super-binary plasmid including vir gene was cultured onto an AB culture plate (AB-t) adding tetracycline (10 mg/L) for 2 to 3 days at 28° C. After 2 days, *E. coli* HB101containing the pRK201, a conjugal helper plasmid and *E. coli* DH-5α containing the pGlb-PIC vector were cultivated onto LB plates adding kanamycin (50 mg/L) and spectinomycin (50 mg/L) respectively at 37° C. overnight so as to collect total 3 kinds of colonies. The 3 kinds of colonies were mixed with an injection loop and cultured onto a nutrient agar plate (Difco) at 28° C. overnight. The resulting bacteria were diluted 10-fold with culture broth (or water), streaked for single cell isolation onto an AB culture plate (AB-st) adding spectinomycin (50 mg/L) and tetracycline (10 mg/L) and cultured for 3 days at 28° C. Single colonies appearing onto the AB culture plate (AB-st) were streaked once more and cultured for 3 days at 28° C. to select a final single colony (*Agrobacterium tumefaciens* LBA4404 pGlb-PIC) if reappearing. The resulting *Agrobacterium* was inoculated into YEP culture broth (YEP-st) adding spectinomycin (50 mg/L) and tetracycline (10 mg/L) and cultured with shaking for 2 days. Then, plasmids were isolated to be analyzed with a pattern of restriction digestion. As a result, it is re-identified that *Agrobacterium* be transformed with pGlb-PIC gene. Next, the *Agrobacterium tumefaciens* LBA4404 pGlb-PIC was used to transform a rice plant.

Example 14

Plant Transformation by *Agrobacterium* and Seed Colors After Harvesting Rice Transformant The same procedure was accomplished as described in Example 5, but the pGlb-PIC vector was used instead of the pGlb-PAC vector to transform rice plant.

As a result, 7 of the re-differentiated rice plants transformed with the pGlb-PIC gene obtained above (PIC-3, 4, 5, 6, 7, 8 and 9) were compared according to density of yellow color in seeds. Because they are re-differentiated at different stages respectively, PIC4, 5, 6, 7 and 8 lines produced beta-carotenes at T2 seeds and PIC3 and 9 lines at T1 seeds were examined to compare a density of yellow color appearing after producing beta-carotenes. After harvested, mature seeds of each line were peeled off with a rice husker (TR-200 Electromotion rice husker, Kett product) and then, polished with a rice polisher for 1 minute to remove aleurone layer (Pearlest polisher, Kett). These polished rice was compared one another.

Figure 10:
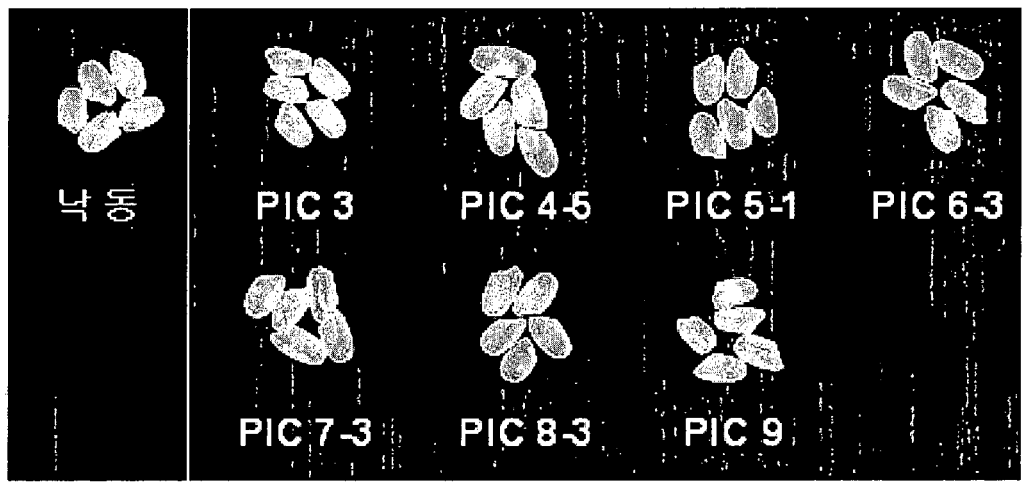
FIG. 10 is T1- and T2-generation mature seeds collected from the rice endosperm that is transformed with the multi-cistronic pGlb-PIC vector of the invention to produce beta-carotenes and appears yellow color.

Therefore, it is observed with naked eyes that PIC8 appear the densest yellow color and PIC4, 5, 6 and 7 appear similar densities of yellow color less than the PIC8. PIC3 and 9 lines, a Ti-generation seed tended to appear less dense yellow color than the T2-generation seeds (See FIG. 10).

Example 15

Separation, PCR Analysis and Southern Blot Analysis of Plant Transformant

Figure 11:
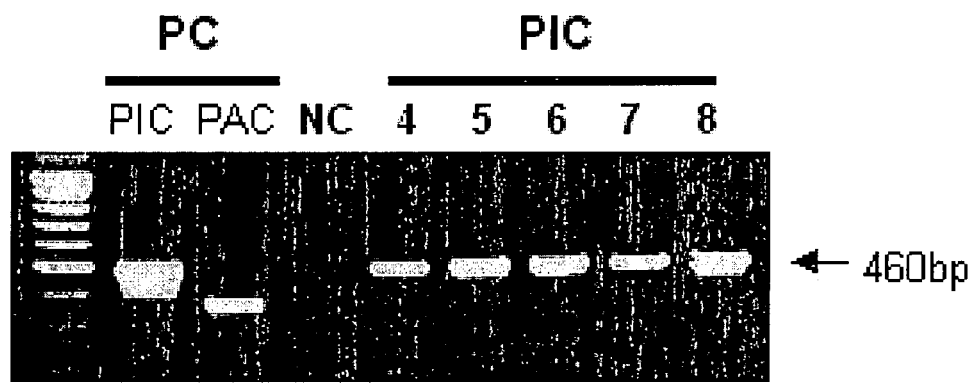
FIG. 11 is a gene insertion of rice plant identified by performing a gel electrophoresis (M: 1 kb ladder of DNA size marker; PC: the pGlb-PIC vector; NC: non-transgenic control rice plant (Nakdong); and 4, 5, 6, 7, 8: T1-generations of rice plant transformed with the pGlb-PIC vector)

Among transformed rice plants, PIC4, 5, 6, 7 and 8 were selected to collect leaf tissues. Then, genomic DNAs were separated and purified by using Genomic DNA Purification Kit (I.J. BIO DNA System). The resulting DNA eluant was quantitated by measuring optical density at A260/A280 with a UV spectrometer. 100 ng of the genomic DNA was used for template and a primer set containing CrTMV-IRES was added in 10 pmol to conduct a PCR reaction. The primer set was composed of Psy-CT-Fw primer of SEQ ID NO: 47 containing C-terminus of Psy gene and CrtI-NT-Rv primer of SEQ ID NO: 48 containing N-terminus of CrtI gene. They were mixed with 10× Taq polymerase buffer (250 μM MgCl$_2$, 100 μM dNTP, 1 unit Taq polymerase (Takara) to be adjusted to 20 μL of total volume, reacted for PCR amplification under the following condition: 95° C. 30 seconds, 55° C. 30 seconds, 72° C. 30 seconds repeatedly for 30 cycles and then extended 72° C. 5 minutes. As a result, 460 bp of the PCR product was identified as expected (See FIG. 11).

Figure 12:
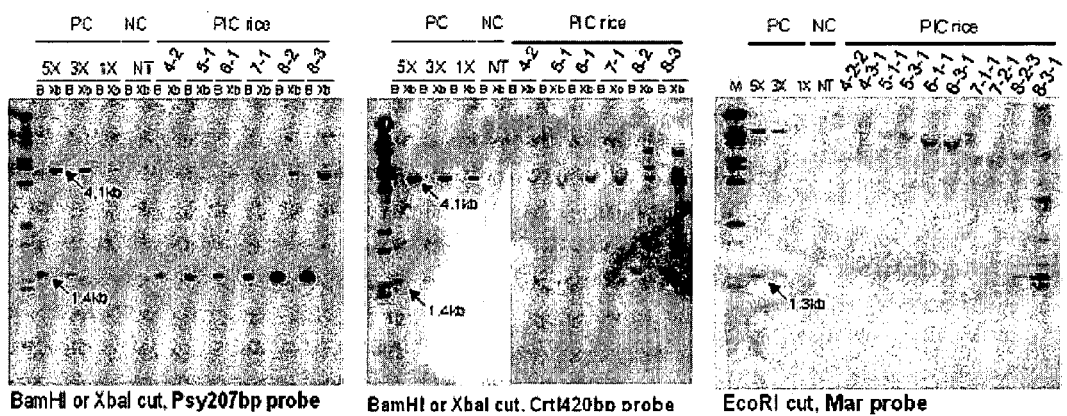
FIG. 12 is a gene insertion and gene copy number identified by performing a genomic Southern blot using chromosomal DNA of rice plant (M: 1 kb ladder of DNA size marker; PC: the pGlb-PIC vector; NC: non-transgenic control rice plant (Nakdong); and 4-2, 5-1, 6-1, 7-1, 8-2, 8-3: T2-generations of rice plant transformed with the pGlb-PIC vector)

The genomic DNAs isolated above were digested in 5 μg of each line with restriction enzyme BamHI and XbaI and analyzed by conducting an agarose gel electrophoresis. Then, 207 bp of $^{32}$P-labelled Psy gene and 420 bp of CrtI gene were used for probes so as to identify gene insertion. 1.4 kb and 4.1 kb of insert genes were detected in PIC4, 5, 6 and 7 excepting PIC8. But in PIC8, at least 3 signal bands were detected when conducting Southern blot with CrtI probe after DNA was digested with restriction enzyme XbaI. Therefore, it is guessed that they may provoke a rearrangement of inserted genes around the CrtI gene. Then in order to calculate a gene copy number, the same genomic DNA was digested in 5 μg with restriction enzyme EcoRI, analyzed by conducting an agarose gel electrophoresis and blotted by using 1.3 kb of $^{32}$P-labelled Mar gene for probe. As a result, PIC5, 6 and 7 showed two Mar signal bands (left border: 1.3 kb of Mar signal band; right border: Mar signal bands different in the size according to insertion sites because rice genomic DNA was digested at an unknown site with restriction enzyme EcoRI) clearly. By using Mar gene for probe, this result proved an insertion of one copy gene. Besides, PIC4 showed a signal pattern expected in case of 2 copy genes. PIC8 showed a signal pattern expected in case of at least more than 3 copy genes (See FIG. 12).

Example 16

RT-PCR Analysis of Plant Transformant

Total RNA was separated from rice harvested in the transformed plant and analyzed to examine an expression of PIC gene according to multi-cistronic sites. In detail, in order to separate total RNA, 1 g rice sample of each line was soaked for about 2 hours, powdered sufficiently using a mixing bowl under a liquid nitrogen and mixed vigorously with 5 mL of RNA extraction buffer [200 mM Tris-HCl (pH 9.0), 400 mM LiCl, 25 mM EDTA (pH 8.2), 1% SDS] and 5 mL of phenol. The mixture was transferred to a 15 mL tube, centrifuged at 3,000 rpm for minutes and supernatant layer was carefully transferred to a fresh tube. Then, 1 mL of chloroform and 1 mL of phenol were added, vortexed and centrifuged again at 3,000 rpm for 10 minutes to collect supernatant. After that, the supernatant was carefully transferred to a fresh tube and vortexed sufficiently after adding 2 mL of chloroform to extract the solution. This procedure was repeated twice. The resulting supernatant was transferred to a fresh tube and stored at –20° C. for an hour after adding 2.5 volume of ethanol and 0.1 volume equivalence of 3 M sodium acetate (pH 5.2). Then, it was centrifuged at 4° C., 12,000 rpm for 10 minutes to collect DNA and RNA pellets, dissolved in 2 M lithium chloride (LiCl) solution and incubated at –20° C. for more than 2 hours to precipitate RNA. The RNA pellet was washed once with 80% EtOH and dissolved 80 to 100 μL of DEPC solution. The RNA extract was quantitated by measuring optical density at A260/A280 with a UV spectrophotometer in order to perform an mRNA selective RT-PCR.

1 μg of the total RNA was used for template and amplified with a commercial kit (Takara mRNA selective RT-PCR kit [1× RT buffer, 5 mM MgCl$_2$, 1 mM dNTP, 50 μM Oligo dT primer, RNase inhibitor (0.1 unit/μL), AMV RTase XL (0.1 unit/μL)] (Takara, Japan). In order to synthesize cDNA, they were reacted at 30° C. for 10 minutes and at 42° C. for 30 minutes and cooled at 4° C. The synthetic cDNA was reacted with following primer sets. Precisely, PST gene-specific primer set of SEQ ID NO: 49 and SEQ ID NO: 50; Tp-CrtI gene-specific primer set of SEQ ID NO: 51 and SEQ ID NO: 52; a primer set specific for 460 bp SL (small-length) of CrTMV-IRES sequence of PIC gene of SEQ ID NO: 47 and SEQ ID NO: 48; a primer set of SEQ ID NO: 53 and SEQ ID NO: 54 amplifying total length of PIC gene; and a rice glutelin specific primer set of SEQ ID NO: 66 and SEQ ID NO: 56 confirming a fixed relative amount of RNA were used to perform a PCR.

Figure 13:
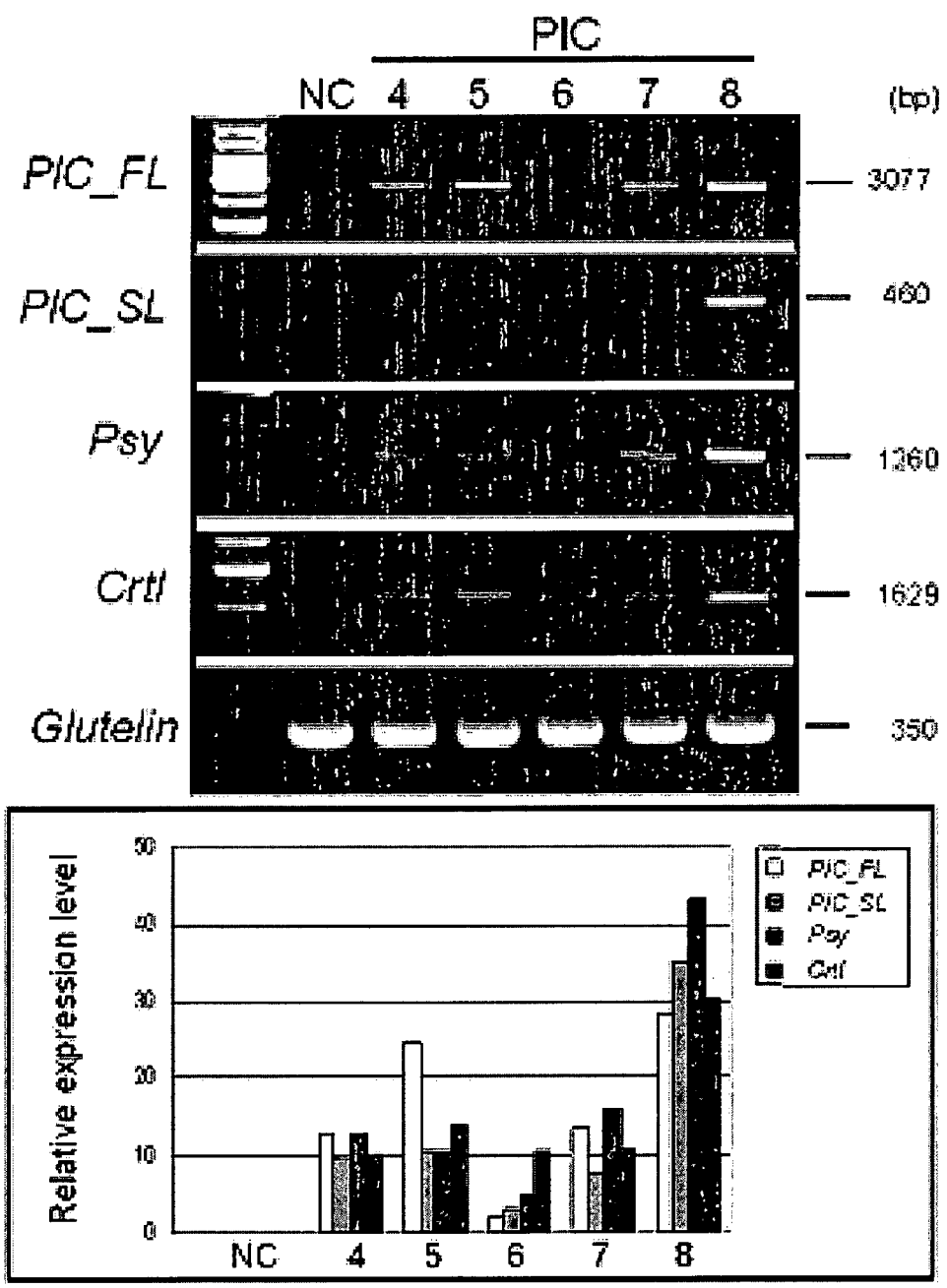
FIG. 13 is a comparison of gene expression patterns of transcripts using total RNA that is isolated from rice plant seeds transformed with the multi-cistronic pGlb-PIC vector after performing a RT-PCR (M: 1 kb ladder of DNA size marker; NC: mature seed of non-transgenic control rice plant (Nakdong); and 4, 5, 6, 7, 8: rice plant seeds transformed with the pGlb-PIC vector)
Figure 14:
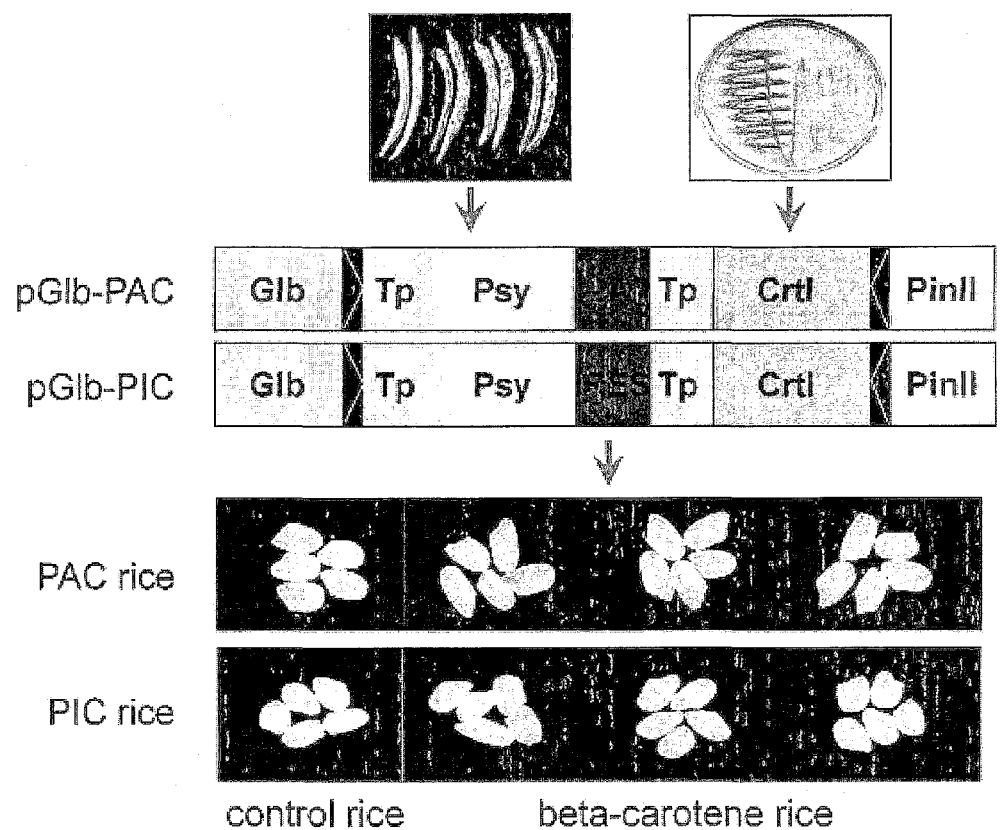
FIG. 14 is mature seeds of the rice plant that are transformed with the multi-cistronic vectors to produce beta-carotene and appears yellow color (Glb: rice endosperm-specific globulin promoter; Tp: chloroplast target transit peptide gene; Psy: phytoene synthase gene derived from Korean pepper NocKgwang; st2A: 2A sequence optimized in a rice plant; IRES: internal ribosomal entry site; CrtI: bacterial carotene desaturase gene; PinII: potato protease inhibitor II terminator).

As a result, all transcripts of Psy gene, CrtI gene, PIC_SL gene, PIC_FL gene were not detected in intact rice seeds (Nakdong), but the all transcripts were clearly detected in transformed rice seeds respectively with expected sizes. When using glutelin as a control group, the degrees of gene expression were compared in 4 sites of the PIC transformant. It is identified that they are similar in all lines excepting PIC8 (See FIG. 13).

Example 17

HPLC Analysis of Seeds of Plant Transformant

Samples of transformed rice were requested to Korea Food Research Institute, an authorized organization for food analysis to perform analysis of beta-carotene [Food Code (2006), Analysis of Trace Nutrients). As a result, as expected, PIC4, 5, 6 and 7 lines were observed to include 183 μg/100 g, 171 μg/100 g, 195 μg/100 g and 206 μg/100 g of beta-carotene in a similar level respectively, but beta-carotene was not detected at all in general rice plant (Nakdong). Therefore, it is identified that beta-carotene was produced in about 0.2 mg per 100 g of rice when introducing the multi-cistronic recombinant PIC gene of the present invention.

INDUSTRIAL APPLICABILITY

As can be seen from the foregoing, fusion polynucleotides and the recombinant vector using the same of the present invention have the effect of expression both phytoene synthase gene and carotene desaturase gene stably within cell transformants. Accordingly, fusion polynucleotides of the present invention can be used to regulate the biosynthetic metabolism of plant producing beta-carotene. Furthermore, it can be applied to effectively increase the content of beta-carotene, a useful metabolite.

The invention claimed is:

1. A recombinant vector comprising a promoter and a fusion polynucleotide for the biosynthesis of beta-carotene comprising the nucleotide sequence as set forth in SEQ ID NO:1 having the phytoene synthase gene of pepper, FMDV-derived 2A sequence optimized in rice plant, and the carotene desaturase gene of bacteria, wherein the recombinant vector is a pGIb-PIC vector or a pGIb-PAC vector.

2. A recombinant vector comprising a promoter and a fusion polynucleotide for the biosynthesis of beta-carotene comprising the nucleotide sequence as set forth in SEQ ID NO:42 having the phytoene synthase gene of pepper, the internal ribosome entry site (IRES) gene, and the carotene desaturase gene of bacteria, wherein the recombinant vector is a pGIb-PIC vector or a pGIb-PAC vector.

3. A transformed cell, which is transformed with a recombinant vector selected from the group consisting of the recombinant vectors according to claim 1 and claim 2.

4. The transformed cell of claim 3, which is *Agrobacterium tumefaciens* or *Agrobacterium rhizogene*.

5. A transformed plant cell, which is transformed with a vector selected from the group consisting of the recombinant vectors according to claim 1 and claim 2 to synthesize β-carotene.

6. A transformed plant, which is transformed with a vector selected from the group consisting of the recombinant vectors according to claim 1 and claim 2 to synthesize β-carotene.

7. A plant of claim 6, which is mono-cotyledonous or di-cotyledonous.

8. A plant of claim 6, wherein the plant is selected from the group consisting of rice plant, wheat, barley, bamboo shoot, corn, taro, asparagus, onion, garlic, welsh onion, scallion, wild rocambole, yam, ginger, *Arabidopsis*, eggplant, tobacco, pepper, tomato, burdock, crown daisy, lettuce, bellflower, spinach, spinach beet, sweet potato, celery, carrot, dropwort, parsley, white cabbage, cabbage, radish, water melon, melon, cucumber, pumpkin, gourd, strawberry, soy bean, mung bean, kidney bean, bird's-foot trefoil, potato, duckweed, green perilla, pigeon pea, narcissus, marigold and green bean.

9. A transformed mushroom, which is transformed with a vector selected from the group consisting of the recombinant vectors according to claim 1 and claim 2 to synthesize β-carotene.

* * * * *